(12) United States Patent
Blonder et al.

(10) Patent No.: US 7,767,197 B2
(45) Date of Patent: Aug. 3, 2010

(54) DELIVERY VEHICLE COMPOSITION AND METHODS FOR DELIVERING ANTIGENS AND OTHER DRUGS

(75) Inventors: Joan P. Blonder, Lafayette, CO (US);
Claire M. Coeshott, Denver, CO (US);
Timothy C. Rodell, Aspen, CO (US);
Wren H. Schauer, Boulder, CO (US);
Gary J. Rosenthal, Louisville, CO (US)

(73) Assignee: Endo Pharmaceuticals Colorado LLC, Chadds Ford, PA (US)

( * ) Notice: Subject to any disclaimer, the term of this patent is extended or adjusted under 35 U.S.C. 154(b) by 1199 days.

(21) Appl. No.: 09/888,235

(22) Filed: Jun. 22, 2001

(65) Prior Publication Data
US 2002/0025326 A1 Feb. 28, 2002

Related U.S. Application Data

(63) Continuation-in-part of application No. 09/602,654, filed on Jun. 22, 2000.

(60) Provisional application No. 60/278,267, filed on Mar. 23, 2001.

(51) Int. Cl.
*A61A 31/745* (2006.01)
*A61A 31/00* (2006.01)

(52) U.S. Cl. .............. 424/78.17; 424/78.18; 424/78.19; 424/78.31; 424/204.1

(58) Field of Classification Search .............. 424/70.11, 424/70.19, 78.31, 78.77, 236.1, 70.15, 70.14, 424/78.17, 78.18, 78.19, 204.1, 234.1, 93.1, 424/93.2
See application file for complete search history.

(56) References Cited

U.S. PATENT DOCUMENTS

| | | | |
|---|---|---|---|
| 4,971,956 A | 11/1990 | Suzuki et al. ................. 514/55 |
| 5,071,644 A | 12/1991 | Viegas et al. ............. 514/772.7 |
| 5,300,295 A * | 4/1994 | Viegas et al. ................ 424/427 |
| 5,593,683 A | 1/1997 | Viegas et al. ................ 424/427 |
| 5,607,691 A * | 3/1997 | Hale et al. .................. 424/449 |
| 5,695,770 A * | 12/1997 | Raychaudhuri et al. .. 424/278.1 |
| 5,702,717 A | 12/1997 | Cha et al. ................... 424/425 |
| 5,709,860 A * | 1/1998 | Raychaudhuri et al. .. 424/184.1 |
| 5,861,174 A | 1/1999 | Stratton et al. ............. 424/484 |
| 5,885,590 A * | 3/1999 | Hunter et al. ............. 424/280.1 |
| 5,902,110 A | 5/1999 | Alfano et al. ............... 433/215 |
| 5,912,000 A | 6/1999 | Podolski et al. ......... 424/278.1 |
| 5,939,485 A | 8/1999 | Bromberg et al. ........... 525/556 |
| 5,980,912 A | 11/1999 | Podolski et al. ......... 424/278.1 |
| 6,004,573 A | 12/1999 | Rathi et al. ................ 424/426 |
| 6,086,899 A | 7/2000 | Balasubramanian et al. ....... 424/280.1 |
| 6,117,949 A | 9/2000 | Rathi et al. ................. 525/415 |
| 6,201,072 B1 | 3/2001 | Rathi et al. ................. 525/415 |
| 6,207,646 B1 | 3/2001 | Krieg et al. ................... 514/44 |
| 6,218,148 B1 | 4/2001 | Zsebo et al. ............... 435/69.5 |
| 6,239,116 B1 | 5/2001 | Krieg et al. ................... 514/44 |
| 6,416,947 B1 * | 7/2002 | Balasubramanian et al. ... 435/5 |
| 2001/0044416 A1 | 11/2001 | McCluskie et al. ............ 514/44 |

FOREIGN PATENT DOCUMENTS

| | | |
|---|---|---|
| EP | 0860 166 A1 * | 8/1998 |
| WO | WO 97/00275 | 1/1997 |
| WO | WO 97/20576 | 6/1997 |
| WO | WO 98/06438 | 2/1998 |
| WO | WO 98/29487 | 7/1998 |
| WO | WO 99/32135 | 7/1999 |
| WO | WO 99/65521 | 12/1999 |
| WO | WO 00/07603 | 2/2000 |
| WO | WO 00/56361 | 9/2000 |
| WO | WO 00/56362 | 9/2000 |
| WO | WO 01/12218 A1 | 2/2001 |
| WO | WO 01/22972 A2 | 4/2001 |

OTHER PUBLICATIONS

Cox et al Vaccine 1997, vol. 15, pp. 248-256.*
Roberts Edelman in Vaccine Adjuvants in Methods in Molecular Medicine 2000, edited by O'Hagan, Humana Press Inc. pp. 1-27.*
Cox et al. Vaccine 1997, vol. 15, No. 3, pp. 248-256.*
Yamamoto et al. Proc. Natal. Acad. Sci. 1997, vol. 94, pp. 5267-5272.*
Encke et al. Intervirology 1999, vol. 42, pp. 117-124.*
Tam et al. J. Hepatology 1999, vol. 30, pp. 376-382.*

(Continued)

*Primary Examiner*—Robert Mondesi
*Assistant Examiner*—Bao Qun Li
(74) *Attorney, Agent, or Firm*—Marsh Fischmann & Breyfogle LLP; Ross E. Breyfogle

(57) ABSTRACT

The present invention provides an immunogen composition and methods for using the same for the development of immunity, and particularly at mucosal sites in a mammal, thereby providing immunity at the site of entry for many major pathogenic organisms and also systemic immunity. The immunogen composition includes an antigen, a biocompatible polymer, and a liquid vehicle, with the biocompatible polymer and liquid vehicle being present in such proportions and interacting in such a way that the immunogen composition exhibits reverse-thermal viscosity behaviour. A delivery vehicle composition including a drug other than an antigen is also provided. Methods are provided for delivering the compositions of the invention to a host.

41 Claims, 12 Drawing Sheets

OTHER PUBLICATIONS

McNickoli et al. AIDS Research and Human Retroviruses 1998, vol. 14, No. 16, pp. 1457-1471.*
Allison A Methods 1999, vol. 19, pp. 87-93.*
Witer et al. Infection and Immunity 1988, vol. 56, No. 11, pp. 2808-2817.*
Coulter Vaccine 1997, vol. 16, No. 11/12, pp. 1243-1253.*
Hunter et al. J. Immunol. 1984, vol. 133, No. 6, pp. 3167-3175.*
Byars et al. Vaccine 1990, vol. 8, pp. 49-56.*
Hunter et al. Vaccine 1991, vol. 9, pp. 250-256.*
Miller et al. Vaccine 1992, vol. 10, pp. 547-550.*
Malakoff, "Aluminum is Put on Trial as a Vaccine Booster," Science, 2000. 288: 1323.
McNeela, E.A. et al. A mucosal vaccine against diphtheria: formulation of cross reacting material (CRM197) of diphtheria toxin with chitosan enhances and systemic antibody and Th2 responses following nasal delivery. 2001. Vaccine 19: 1188-1198.
Seferian, P.G. and M.L. Martinez. Immune stipulating activity of two new chitosan containing adjuvant formulations. 2001. Vaccine 19: 661-668.
Edelman, R., An Overview of Adjuvant Use, in "Vaccine Adjuvants" Ed. D.T. O'Hagan, Humana Press, Totowa, NJ. 2000. 1-27.
Baldrige, J. R. et al. Monophosphoryl lipid A enchances mucosal and systemic immunity to vaccine antigens following intranasal administration. 2000. Vaccine 18: 2416-2425.
Goto, N. et al. Safety evaluation of recombiant cholera toxin B subunit produced by *Bacillus brevis* as a mucosal adjuvant. 2000. Vaccine 18: 2164-2171.
McCluskie, M. et al. Intranasal Immunization of Mice with CpG DNA Induces Strong Systemic and Mucosal Responses That Are Influenced by Other Mucosal Adjuvants and Antigen Distribution. 2000. Mol. Med. 6: 867-877.
Bacon, A. et al. Carbohydrate biopolymers enchance antibody responses to mucosally delivered antigens. 2000. Infection and Immunity. 68: 5784-5770.
Witschi, C. and R.J. Mrsny. In vitro Evaluation of Microparticles and Polymer Gels for Use as Nasal Platforms for Protein Delivery. 1999. Pharmaceutical Research 16: 382-390.
Barchfield G.L. et al. The adjuvants MF59 and LT-K63 enhance the mucosal and systemic immunogencity of subunit influenza vaccine administered internasally in mice. 1999. Vaccine 17: 695-704.
Isaka, M. et al. Systemic and mucosal immune responses of mice to aluminum-adsorbed or aluminum-non-adsorbed tetanus toxoid administered intranasally with recombinant cholera toxin B subunit. 1998. Vaccine 16: 1620-1626.
Jabbal-Gill et al. Stimulation of mucosal and systemic antibody response against *Bordatella pertussis* flilamentous haemagglutinin and recombinant pertussis toxin after nasal administration with chitosan in mice. 1998. Vaccine 16: 2039-2046.
Horner, A.A. et al. Immunostimulatory DNA is a Potent Mucosal Adjuvant. 1998. Cell. Immunol. 190: 77-82.
Lowrey, L. et al. Induction of Tolerance via the Respiratory Mucosa. Int. Arch. Allergy Immunol. 1998. 116: 93-102.
Yamamoto, S. et al. A nontoxic mutant of cholera toxin elicits Th2-type responses for enhanced mucosal immunity. 1997. Proccedings of the National Academy of Sciences of the United States of America. 94: 5267-5272.
Neutra, M.R. et al. Antigen Sampling Across Epithelial Barriers and Induction of Mucosal Immune Responses. 1996. Ann. Rev. Immunol. 14: 275-300.
Levi, R. et al. Intranasal immunization of mice against influenza with synthetic peptides anchored to proteosomes. 1995. Vaccine: 13: 1353-1359.
Pizza, M. et al. A Genetically Detoxified Derivative of Heat-labile *Escherichia coli* Enterotoxin Induces Neutralizing Antibodies Against the A Subunit. 1994. J. Exp Med 180, 2147-2153.
Illum, L. et al. Chitosan as a Novel Nasal Delivery System for Peptide Drugs. 1994. Pharmaceutical Research 11: 1186-1189.
Tamura, S. et al. Synergistic action of cholera toxin B subunit (and *Escherichia coli* heat-labile toxin B subunit) and a trace amount of cholera whole toxin as an adjuvant for nasal influenza vaccine. 1994. Vaccine 12: 419-426.
Holmgren, J. et al. Cholera toxin and cholera B subunit as oral-mucosal adjuvant and antigen vector systems. 1993. Vaccine 11: 1179-1184.
McGhee, J.R. et al. The mucosal immune system: from fundamental concepts to vaccine development. 1992. Vaccine: 10: 75-88.
McNicholl, J.M. et al. Enhancement of HIV Type 1 Vaccine Immunogenicity by Block Copolymer Adjuvants. I. Induction of High-Titer, Long-Lasting, Cross-Reactive Antibodies of Broad Isotype, AIDS Research and Human Retroviruses, vol. 14, No. 16, 1998, pp. 1457-1471.
Raghuvanshi, R.S. et al. Biodegradable delivery system for single step immunization with tetanus toxoid. International Journal of Pharmaceutics. 1993. 93: R1-R5.
Lemieux, P. et al., A combination of poloxamers increases gene expressions of plasmid DNA in skeletal muscle, Gene Therapy, 2000, vol. 7, pp. 986-991.
Miyazaki, S. et al., Sustained-Release and Intragastric-floating Granules of Indomethancin Using Chitosan in Rabbits, Chem. Pharm. Bull, 1998 vol. 36 (10), pp. 4033-4038.
Newman, M. J. et al., "Development of Adjuvant-Active Nonionic Block Copolymers"; Advanced Drug Delivery Reviews 32 (1998) 199-223.
Reed, C. "Pluronic Block Copolymers As Immunological Adjuvants", A Thesis Submitted For The Degree Of Doctor Of Philosophy, Jan. 1993, Dept. of Parmaceutical Sciences, University of Strathclyde.
Spitzer, N. et al., "Long-Term Protection of Mice Against *Leishmania Major* With A Synthetic Peptide Vaccine,"; Vaccine 17 (1999) (1298-1300).

* cited by examiner

DELIVERY VEHICLE COMPOSITION AND METHODS FOR DELIVERING ANTIGENS AND OTHER DRUGS

CROSS REFERENCE TO RELATED APPLICATIONS

This application is a continuation-in-part under 35 U.S.C. §120 of nonprovisional U.S. patent application Ser. No. 09/602,654 entitled "IMMUNOGEN COMPOSITION AND METHODS FOR USING THE SAME" filed Jun. 22, 2000, the entire contents of which are incorporated herein by reference as if set forth herein in full. This application claims a priority benefit under 35 U.S.C. §119(e) to provisional U.S. Patent Application No. 60/278,267 entitled "IMMUNOGEN COMPOSITION AND METHODS FOR DELIVERY OF ANTIGEN TO ELICIT MUCOSAL IMMUNE RESPONSE" filed Mar. 23, 2001, the entire contents of which are incorporated herein by reference as if set forth herein in full.

FIELD OF THE INVENTION

This invention relates to a delivery vehicle composition for delivery of an antigen or another active material and methods for using such a delivery vehicle composition, and especially for stimulating an immune response both systemically and mucosally.

BACKGROUND OF THE INVENTION

Ideally, an immunogen composition should potentiate long-lasting expression of functionally active antibodies, elicit cell-mediated immunity ("CMI"), and enhance production of memory T- and B-lymphocytes with highly specific immunoreactivity against an invading antigen. In addition to providing a defense upon immediate challenge with a foreign antigen, these responses should provide protection against any future encounters of the host with a specific antigen.

Situations in which it is desirable to elicit these types of sustained responses include the development of protective immunity against infectious agents or their products, against tumor antigens for the treatment of cancer and as a form of sterilization or birth control in which an immune response is induced against components of the mammalian reproductive system such as human chroionic gonadotrophin (HCG). The complexity of the immune system in mammals is well established and many factors contribute to the type of immune response that occurs when a foreign substance is encountered. Three outcomes are possible: it may be ignored, it may induce a state of unresponsiveness or tolerance such that a future encounter with that antigen would not result in an immune response or it may elicit an immune response the quality of which is influenced by the many factors. These include the form of the antigen, whether soluble or particulate in nature, the foreignness of the antigen, i.e., how far removed the antigen is from the host on the phylogenetic tree, the stability of the antigen to degradative enzymes of the host and the ability of the antigen to persist in the host for long periods of time. It can be appreciated that the immunogenicity of an antigen that elicits a weak immune response may be improved by manipulation of one or more of these parameters.

Traditionally the immunogenicity of an antigen has been improved by injecting it in a formulation that includes an adjuvant. Adjuvants non-specifically augment immune responses and their ability to potentiate immune responses has long been recognized. A wide variety of substances, both biological and synthetic, have been used as adjuvants in experimental systems. These include mycobacteria, oil emulsions, liposomes, polymer microparticles and mineral gels. The mechanism by which adjuvants enhance immune responses is not uniform but their effects may include retention of antigen at the site of administration such that the antigen is released to the body slowly over time or array of the antigen in a particulate form so that it is more easily recognized by lymphocytes and taken up by antigen presenting cells. Adjuvants consisting of microbial products generally act by enhancing the uptake of antigens by professional antigen-presenting cells and/or by stimulation of the innate immune system, which in turn leads to more potent stimulation of lymphocytes themselves.

For therapeutic use in humans, however, the toxic side effects of many adjuvants used as research tools have limited their use. Currently only aluminum salts are approved for use in humans in the United States and these are a component of many common vaccines, e.g., tetanus and DTP. However, there is some concern regarding the safety of aluminum salts (Malakoff, "Aluminum is Put on Trial as a Vaccine Booster," *Science,* 2000, 288, 1323). When aluminum salts are used as an adjuvant, the antigen is adsorbed to the aluminum salt, thereby arraying the antigen in particulate form as well as forming a depot of antigen, which is released slowly over time. Even in this formulation, however, vaccines are usually administered several times over a time span of months in order to elicit an immune response that can confer protection on the host upon subsequent encounter with the antigen, e.g., microbe, itself. Thus although vaccines for a variety of infectious diseases are currently available, many of these, including those for tetanus and hepatitis B, require more than one administration to confer protective benefit. These limitations are extremely problematic in countries where healthcare is not readily available or accessible. Moreover, compliance is also a problem in developed countries, particularly for childhood immunization programs. For example, a child in the United States may be scheduled to receive a total of 16 vaccine injections by age 18 months and 35 vaccine injections by age five.

Research efforts into improving vaccines have developed along many different but parallel courses but of great importance have been the development of new compositions and delivery systems, which could reduce the number of injections, required but still elicit long-lasting protective immunity. Included in this are the development of new and novel adjuvants with improved safety profiles. In research efforts to reduce the immunization regimens research has been directed towards both development of single dose delivery vehicles and development of non-injectable vaccines.

Mucosal vaccine strategies have recently emerged as an attractive potential alternative to injectable vaccines. Mucosal administration would have many potentially desirable attributes. This form of administration is relatively easy and low cost, especially when compared to injection regimens. As such, mucosal administration has significant potential to improve compliance in both developing and developed countries relative to vaccine injections, particularly for childhood immunization programs. Another advantage of mucosal administration compared to injection is a reduced risk of contamination with elimination of the use of needles.

Perhaps the most compelling reason for developing mucosal vaccine delivery techniques, however, is development of a first line of immunity defense, by generating local immunity at the mucosal site of entry for many invading pathogens. Moreover some investigators have reported that a common mucosal immune system exists, whereby mucosal immunity induced at one site can lead to immunity at a distal mucosal site (McGhee, J. R. et al. The mucosal immune system: from fundamental concepts to vaccine development. *Vaccine* 1992, 10:75-88). This suggests that significant benefits can be achieved by the delivering of vaccines in a non-invasive way, e.g. intranasally or other mucosal route, to elicit immunity to a wide range of pathogens that may enter at different mucosal sites, e.g. HIV, HPV. In addition, delivery of an antigen via a mucosal site has the potential to generate a systemic immune response as well.

A mucosal immune response consists of all the components of the systemic immune system including the ability to generate cell-mediated and humoral responses. Cells of the immune system are distributed throughout mucosal tissues and include T and B cells and cells capable of antigen presentation, such as dendritic cells and monocytes/macrophages (Neutra, M. R. et al. Antigen sampling across epithelial barriers and induction of mucosal immune responses. 1996. *Ann. Rev. Immunol.* 14: 275-300). The main antibody class present in the mucosal immune system is IgA, which is exported in polymeric form into mucosal secretions. Once in the lumen, IgA antibodies prevent attachment of infectious agents or their toxins to mucosal epithelia thereby providing a first line of defense against infection. Detection of IgA antibodies in washes of mucosal surfaces indicates the generation of a mucosal immune response to an antigen.

Although there is great promise for mucosal administration of vaccines, delivery of many antigens, such as proteins and peptides, to the mucosal tissue does not necessarily result in the generation of an immune response. The generation of mucosal immunity to antigens is dependent upon the same criteria as is the systemic immune response, namely that the antigen must be presented appropriately in a form that will lead to stimulation of T and B lymphocytes. This often means that an adjuvant is required to non-specifically enhance the mucosal immune response as well as the systemic response. In addition to this requirement, uptake of antigens from the mucosae requires that the antigen is able to penetrate the epithelial barrier and gain access to the underlying lymphoid tissue. For these reasons mucosal delivery of antigens may result in low bioavailability and also may induce immunological tolerance (e.g. Lowrey, J. L. et al. Induction of tolerance via the respiratory mucosa. *Int. Arch. Allergy Immunol.* 1998, 116: 93-102).

In recent years many adjuvants and delivery systems have been evaluated for their ability to enhance the immune response to mucosally administered antigens. These include bacterially-derived products such as monophosphoryl lipid A (Baldridge, J. R. et al. Monophosphoryl lipid A enhances mucosal and systemic immunity to vaccine antigens following intranasal administration. 2000. *Vaccine* 18: 2416-2425), immunostimulatory DNA sequences (Homer, A. A. et al. Immunostimulatory DNA is a potent mucosal adjuvant. 1998. *Cell. Immunol.* 190: 77-82; McCluskie, M. J. et al. Intranasal immunization of mice with CpG DNA induces strong systemic and mucosal responses that are influenced by other mucosal adjuvants and antigen distribution. 2000. *Mol. Med.* 6:867-877), outer membrane proteins of *Neiserria meningitidis* serogroup B (Levi, R. et al. 1995. Intranasal immunization of mice against influenza with synthetic peptides anchored to proteosomes. *Vaccine* 13: 1353-9), and bacterial toxins such as cholera toxin (CT) subunit B and *E. coli* enterotoxin (ET) (Isaka, M. et al. Systemic and mucosal immune responses of mice to aluminum-adsorbed or aluminum-non-adsorbed tetanus toxoid administered intranasally with recombinant cholera toxin B subunit. 1998, *Vaccine* 16: 1620-1626; Holmgren, J. et al. Cholera toxin and cholera B subunit as oral-mucosal adjuvant and antigen vector systems.1993 *Vaccine* 11: 1179-1184; Tamura, S. et al. Synergistic action of cholera toxin B subunit (and *Escherichia coli* heat-labile toxin B subunit) and a trace amount of cholera whole toxin as an adjuvant for nasal influenza vaccine 1994, *Vaccine* 12: 419-426; Goto, N. et al. Safety evaluation of recombinant cholera toxin B subunit produced by Bacillus brevis as a mucosal adjuvant. 2000. *Vaccine* 18: 2164-2171; and Barchfeld, G. L. et al. The adjuvants MF59 and LT-K63 enhance the mucosal and systemic immunogenicity of subunit influenza vaccine administered intranasally in mice. 1999. *Vaccine* 17: 695-704). However, the inherent toxicity of bacterial toxins generally precludes their use in human vaccines. Detoxified mutants of both CT and ET have been produced (Pizza, M., et al. A genetically detoxified derivative of heat-labile Escherichia coli enterotoxin induces neutralizing antibodies against the A subunit. 1994. *J Exp Med* 180, 2147-53; Yamamoto, S., et al. A non-toxic mutant of cholera toxin elicits Th2-type responses for enhanced mucosal immunity. 1997. *Proceedings of the National Academy of sciences of the United States of America* 94, 5267-72) but these are generally less effective than the wild type toxins. Therefore, the development of novel mucosal vaccine delivery systems that do not induce systemic side effects or damage the mucosal membrane is of prime importance.

A substantial research effort has also been devoted to the improvement of vaccine delivery systems for injectable formulations (see Edelman, R. in "Vaccine Adjuvants" ed. D. T. O'Hagan, Humana Press, Totowa, N.J., 2000). These include microparticles, bacterial products, slow release polymers and other vehicles.

One product in which there has been a lot of recent interest for both mucosal delivery of vaccines and drugs as well as for use as a systemic adjuvant is chitosan, a cationic biopolymer derived from deacetylated chitin. Chitosan has been shown to act as a penetration enhancer to the extent its presence appears to improve the uptake of at least some drugs through the nasal mucosa. The mechanism of action is not completely understood but is thought to be due to opening of the tight junctions between cells in the nasal epithelium as well as increasing residence time of the drug within the nasal passages (Illum, L. et al. Chitosan as a novel nasal delivery system for peptide drugs. 1994. *Pharmaceutical Research* 11: 1186-1189). Chitosan formulated with other excipients such as lysophosphatidylcholine has also been shown to further enhance uptake of proteins across epithelia (Witschi, C. and R. J. Mrsny. In vitro evaluation of microparticles and polymer gels for use as nasal platforms for protein delivery. 1999, *Pharmaceutical Research.* 16: 382-390). In addition, chitosan has been shown to have pro-inflammatory activity, activating macrophages and stimulating secretion of pro-inflammatory cytokines such as $TNF\alpha$ and $IL1\beta$ from monocytes in vitro. Therefore it appears to act as an immunological adjuvant in at least some circumstances. These properties of chitosan have been exploited in the development of vaccines for both intransal and systemic (e.g. intraperitoneal) delivery (McNeela, E. A. et al. 2001. A mucosal vaccine against diphtheria: formulation of cross reacting material (CRM197) of diphtheria toxin with chitosan enhances local and systemic antibody and Th2 responses following nasal delivery. *Vaccine* 19: 1188-1198; Bacon, A. et al. Carbohydrate biopolymers enhance antibody responses to mucosally delivered antigens. *Infection and Immunity* 2000 68: 5764-5770; Jabbal-Gill, I. et al. Stimulation of mucosal and systemic antibody response against *Bordatella pertussis* filamentous haemagglutinin and recombinant pertussis toxin after nasal administration with chitosan in mice. *Vaccine* 16: 2039-2046; and Seferian, P. G. and M. L.

Martinez. Immune stimulating activity of two new chitosan containing adjuvant formulations. *Vaccine*. 2001, 19: 661-668.). However, reports have commented on the intragroup variation occurring when chitosan is used systemically (Jabbal-Gill, I. et al. *Vaccine* 16: 2039-2046) and others have found that further formulation of antigen and chitosan within an emulsion raises more potent antibody responses than a mixture of antigen/chitosan alone (Seferian, P. G. and M. L. Martinez. *Vaccine* 2001. 19: 661-668.).

Although improvements have been made in the area of vaccines there is still a strong need to develop immunogen formulations that reduce or eliminate the need for a prolonged injection regimen. There is also a need to develop immunogen formulations that are well suited for mucosal delivery and that are effective for providing mucosal as well as systemic immunity. There is a further need for immunogen formulations that enhance mucosal immunity locally and systemically with no or reduced side effects and that are administrable without altering the integrity of the mucosal membrane.

SUMMARY OF THE INVENTION

The present invention provides a delivery vehicle composition for delivery of a drug and methods for administering the delivery vehicle composition to effect a desired biological response in the host. The delivery vehicle composition comprises at least one drug, at least one biocompatible polymer and at least one liquid vehicle, with the polymer and the liquid vehicle being of such a type and being present in such proportions that the delivery vehicle composition exhibits reverse-thermal viscosity behavior, meaning that the viscosity of the composition increases with increasing temperature over at least some temperature range. The delivery vehicle composition also typically includes at least one additive selected from the group consisting of an adjuvant, a penetration enhancer and combinations thereof.

The delivery vehicle composition is such that it will typically be administered to the host in the form of a flowable medium at a temperature below the physiological temperature of the host. The viscosity of the composition then increases as the composition is warmed inside the host, and preferably the composition converts to a substantially immobile gel form so that the composition is retained at the desired location for delivery of the drug.

The delivery vehicle composition is administerable to a host in any convenient way for example by injection or direct application to the desired site. One advantage of the delivery vehicle composition, however, is that it is particularly well suited for mucosal delivery. In one preferred embodiment for mucosal delivery, the delivery vehicle composition is in the form of dispersed droplets in a mist. For many mucosal routes, such as, for example, intranasal, sublingual, oral administration, the mist is introduced into the appropriate cavity of administration. Such a mist is typically generated by a nebulizer.

The delivery vehicle composition is exemplified herein by an immunogen composition of the invention in which the drug is an antigen for stimulating an immune response, and preferably without the use of adjuvants, such as alum, of questionable safety. It should be understood, however, that the principles concerning formulation reverse-thermal viscosity behavior and administration, and concerning other attributes of the immunogen composition, also apply for incorporating and using a different type of drug in the delivery vehicle composition.

In the immunogen composition, the biocompatible polymer helps to protect the antigen from possible degradation and to promote prolonged release of the antigen into the host following administration. A preferred liquid vehicle is water or another aqueous liquid and the biocompatible polymer is typically a reverse-thermal gelation polymer, with polyoxyalkylene block polymers being particularly preferred.

In one embodiment, the biocompatible polymer is dissolved in the liquid vehicle when the temperature of the immunogen composition is at some temperature or temperatures below the physiological temperature of the host (approximately 37° C. for humans) so that the biocompatible polymer/liquid vehicle solution is in the form of a flowable liquid. In this situation, the antigen is also preferably dissolved in the liquid vehicle along with the biocompatible polymer. Alternatively, the antigen may be in the form of a particulate suspended in the biocompatible polymer/liquid vehicle solution. In either case, the composition should be in the form of a flowable medium sufficient for nebulization to produce a spray and/or for injectability.

In another embodiment, the immunogen composition is in the form of a gel (semi-solid gelatinous substance) when the composition is at the physiologic temperature of the host (approximately 37° C. for humans). The gel is formed by the interaction between the polymer and the liquid vehicle. For enhanced performance, the antigen should be uniformly dispersed throughout the gel, which is preferably accomplished by initially preparing the immunogen composition at a temperature at which the polymer is dissolved in the liquid vehicle. The antigen can be dissolved in or uniformly dispersed throughout the solution, and then the temperature of the composition can be raised to convert the immunogen composition to a gel form.

In a preferred embodiment, the immunogen composition exhibits reverse-thermal gelation properties, in that the polymer, as incorporated in the immunogen composition, has a gel-liquid transition temperature such that the biocompatible polymer is in solution in the liquid vehicle of some temperature below the transition temperature and the biocompatible polymer and liquid vehicle form a gel, i.e., become gelatinous, as the temperature is raised above the transition temperature. Such a gel-liquid transition temperature may be referred to as a reverse-thermal liquid-gel transition temperature. The reverse-thermal liquid-gel transition temperature should typically be below, and more preferably just below, the physiological temperature of the host. In this way, the composition is administerable to a host at a temperature at which the composition is in the form of a flowable medium and after administration the immunogen composition then converts to a gel form as it warms inside the host to above the transition temperature. The composition can be placed in a syringe or syringe-like device then administered to the host and it can also be placed in a spray device and administered to the host. The immunogen composition preferably has an affinity to adhere to mucosal surfaces, and conversion to a gel form helps to immobilize the immunogen composition at the mucosal surface to retain the antigen in the vicinity of the mucosal surface, thereby permitting the antigen to be effectively delivered to penetrate the mucosal tissue to induce the desired immune response.

In another embodiment, the biocompatible polymer is bioadhesive, so that when the immunogen composition is contacted with a mucosal surface, at least a portion of the biocompatible polymer readily adheres to the mucosal surface. Preferably, the biocompatible polymer and the antigen are closely associated with each other in the immunogen composition so that when the biocompatible polymer adheres to a mucosal surface, the antigen is held in the vicinity of the surface for effective delivery of the antigen across the mucosal epithelium. This will typically be the case, for example, in a preferred embodiment when the carrier liquid is an aqueous liquid and the biocompatible polymer has surfactant properties.

In yet another embodiment, the immunogen composition comprises, in addition to the biocompatible polymer and the antigen, a penetration enhancer that aids rapid transport of the composition across the mucosal epithelium. Furthermore, in at least some instances, the penetration enhancer has been found to improve the immune response following administration of the immunogen composition. Not to be bound by theory, it is believed that the combination of the penetration enhancer and the polymer provide for significant protection of the antigen from degradation and promote release of the antigen from the composition in an advantageous manner.

In yet another embodiment the immunogen composition includes an adjuvant to nonspecifically enhance the immune response. A particularly advantageous aspect of the present invention is that adjuvant-type enhancements are achievable without the use of alum or other known adjuvant materials of questionable safety. In one preferred embodiment, an additive is included in the immunogen composition that acts as both a penetration enhancer and adjuvant, with chitosan materials being particularly preferred for use as the additive for this purpose.

In one surprisingly advantageous embodiment of the present invention, the immunogen composition is administrable mucosally to stimulate both a strong mucosal immune response and also a strong systemic immune response. In this way, the immunogen composition provides the added immunity protection at the site for entry for many major pathogenic organisms, as a first line of defense against and infection by such organisms. The use of the immunogen composition, therefore, has the potential to replace current injection regimens that are effective at developing only systemic immunity, and are not effective at developing mucosal immunity. Also, the immunogen composition has been found to be particularly advantageous for developing rapid, high levels of immunity when delivered non-mucosally and with fewer administrations than has traditionally been the case with conventional multiple injection regimens. In one embodiment, sufficient immunization is achievable with only a single administration of the immunogen composition.

In another aspect, the invention provides a method for delivering the immunogen composition to a host. In one embodiment, a method for administering an antigen to a host to induce a systemic immune response comprises administering the immunogen composition to a host by injection. In another embodiment, a method for administering an antigen to a host to induce a mucosal immune response comprises administering the immunogen composition to a host, preferably by intranasal administration, such as from a nebulizer, syringe, catheter, bulb or other device. In a preferred embodiment, the composition is administered in the form of a flowable medium in which at least the polymer, and optionally also the antigen, is dissolved in the liquid carrier. In a particularly preferred embodiment, the immunogen composition converts to a gel form, which is substantially not flowable, inside the host following administration. This is accomplished, for example, when the polymer, as formulated in the composition, exhibits reverse-thermal gelation properties with a reverse-thermal liquid-gel transition temperature that is at or below the physiologic temperature of the host. In one embodiment, a host is administered one or more, but preferably only one, mucosal administration after having already received a systemic administration of the same antigen in the same or different composition, with the mucosal administration(s) eliciting a mucosal immune response sufficient to provide the host with mucosal immunity to at least one pathogen without disturbing the integrity of the mucosal membrane. This is particularly advantageous for both boosting systemic immunity and stimulating mucosal immunity for the large population group that has already been systemically immunized by injection, but that would benefit from a systemic immunization boost and/or the added first line defense of mucosal immunity. In another embodiment the host is administered one or more mucosal applications of the immunogen composition to elicit an immune response without having previously received a systemic administration. This is particularly advantageous for replacement of injection regimens for hosts that are being initially immunized, and to also provide the hosts with both systemic and mucosal immunity.

In another aspect, the invention provides a method for manufacturing an immunogen composition in which the antigen is dissolved in or dispersed throughout a solution of the polymer dissolved in the liquid vehicle. In yet another aspect, the present invention provides a method for packaging and storing an antigen in the protective environment of the immunogen composition. Handling and storage may be in a gel or liquid form, as desired.

Both the foregoing summary description and the following detailed description are exemplary and explanatory and are intended to provide explanation of the invention as claimed. Other aspects, advantages and novel features will be readily apparent to those skilled in the art from the following detailed description of the invention.

DETAILED DESCRIPTION

Figure 1:
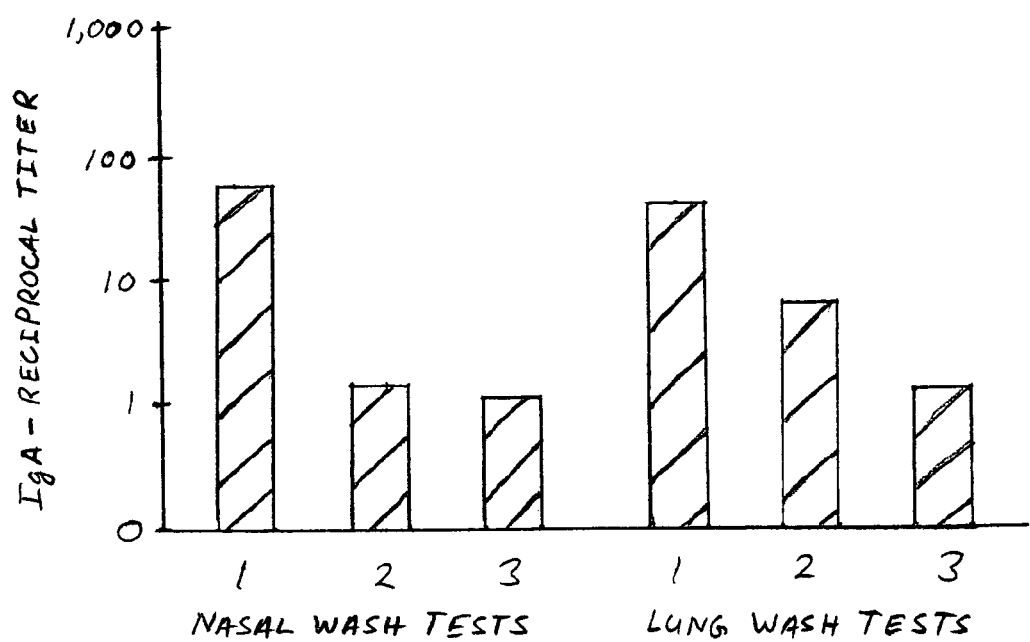
FIG. 1 is a graph of IgA anti-tetanus toxoid (TT) antibody response measured in the lung and nasal washes of inbred mice immunized intraperitoneally (i.p.) with 1.5 LfTT in PBS at day 0 and boosted intranasally (i.n.) 4 weeks later with 1.5 LfTT/F127/chitosan or F127/chitosan without TT (vehicle control). A group of mice is also immunized and boosted i.p with 1.5 LfTT in PBS as a control.

As used herein, "transition temperature" and "liquid-gel transition temperature" each refer to a temperature at which, or a temperature range across which, a material, such as a biocompatible polymer or the immunogen composition as the case may be, changes physical from a liquid form to a gel, or vice versa.

The term "thermal gelation property" refers to a property of a material, such as the polymer or the immunogen composition as the case may be, to change physical form from a liquid to a gel, or vice versa, due to a change in temperature.

The term "reverse-thermal gelation property" refers to a property of a material, such as the polymer or the immunogen composition as the case may be, to change from a liquid to gel form as the temperature is raised from below to above a transition temperature.

The terms "reverse thermal viscosity property" and "reverse thermal viscosity behavior" each refer to a property of a material, such as the polymer or the immunogen composition as the case may be, to undergo a viscosity increase with increasing temperature across at least some temperature range.

The term "reverse-thermal gelation polymer" refers to a polymer capable of interacting with a liquid vehicle so that the polymer/liquid vehicle combination exhibits a reverse-thermal gelation property at least at some proportions of the polymer and the liquid vehicle.

The term "antigen" refers to any material that is capable under appropriate conditions of causing an immune response in a host. Exemplary antigens include polypeptides, peptides, proteins, glycoproteins and polysaccharides that are obtained from animal, plant, bacterial, viral, protozoan and parasitic sources or are produced by synthetic methods, including epitopes of proteins.

The terms "immunogen" and "immunogen composition" as used herein refer to a composition formulated with an antigen for administration to a host in order to elicit an immune response in the host.

As used herein, a "penetration enhancer" refers to any substance or material that assists or aids in the uptake of a drug across a mucosal surface. In the case of an antigen, a "penetration enhancer" assists in moving an antigen across a cellular membrane increasing the likelihood of the antigen reaching its target.

As used herein, an "adjuvant" refers to any substance or material that assists or aids the performance of a drug. In the case of an antigen, an "adjuvant" is a material that nonspecifically enhances or stimulates an immune response to the antigen.

As used herein, "mucosal immunity" and "mucosal immune response" each means an immune response that is generated at least at one mucosal site (e.g. sublingual, buccal, oral, aural, ocular, intranasal, gastrointestinal, pulmonary, vaginal or rectal).

As used herein, "biocompatible" means not having toxic or injurious effects on biological function in a host.

As used herein, "nebulization" means formation, in any manner and by any technique, of a spray or mist of dispersed droplets, such as droplets including the immunogen composition of the present invention, and a "nebulizer" is any apparatus capable of producing such a spray or mist. "Spray" and "mist" are used interchangeably to refer to a dispersion of fine droplets or particles in a carrier gas. The carrier gas may be any gas, such as for example air or a non-air propellant gas exiting a nebulizer.

As used herein, "bioadhesive" means having an affinity to adhere to a biological surface, such as for example mucous membranes or other tissues, for an extended period of time.

The immunogen composition of the present invention typically includes at least one antigen, at least one biocompatible polymer, and at least one liquid vehicle and exhibits reverse thermal viscosity behavior over at least some temperature range. The immunogen composition may optionally also include other components that may enhance performance of the composition.

In one embodiment, the immunogen composition is in the form of a flowable medium, while in another embodiment the immunogen composition is in the form of a gel. In either case, the antigen should be homogenously dispersed throughout the composition. In a preferred embodiment, the immunogen composition is capable of converting from the gel form to the flowable medium form, and vice versa, by a change in temperature across a reverse-thermal liquid-gel transition temperature, so that the immunogen composition is in the form of a flowable medium below the transition temperature and a gel form above the transition temperature. As used herein, a medium is "flowable", when it has sufficiently low viscosity to be syringable and/or nebulizable, depending upon the specific application. Such a flowable medium may, for example, be in a liquid form, or may include a liquid in which fine particulate material is suspended, with the medium retaining sufficient fluidity to be syringible and/or nebulizable.

When the immunogen composition is in the flowable medium form, the biocompatible polymer will typically be substantially all dissolved in the liquid vehicle, and the antigen will also preferably be substantially all dissolved in the liquid vehicle along with the biocompatible polymer. Alternatively, some or all of the antigen may be in the form of a fine particulate, such as a fine precipitate, dispersed throughout the biocompatible polymer/liquid vehicle solution. When present, other components are dissolved in the liquid vehicle or are otherwise preferably uniformly dispersed throughout the composition. When the immunogen composition is in a gel form, the antigen, and other components, when present, will preferably be uniformly dispersed throughout the gel.

The immunogen composition of the present invention is useful for delivering an antigen to a host to treat or prevent an infectious disease. For example, one skilled in the art can readily discern that a microbial infection can be prevented by administering an antigen corresponding to that organism to a host animal as a vaccine to elicit a protective immune response. The host is typically a mammal, and more typically a human. Furthermore, the immunogen composition can be used for the treatment of cancers such as those caused by human papilloma virus. Also, the immunogen composition can be used to alter the mammalian reproductive cycle. Antigens useful in the immunogen composition of the present invention include antigens from bacteria, protozoa and viruses that invade their host via a mucosal surface. Other useful antigens include causative agents of childhood illnesses, antigens from rotavirus, hookworm, *Neisseria meningitiditis, Streptococcus pneumoniae, Bordatella pertussis, M. tuberculosis*, Epstein-Barr virus, Hepatitis C virus, HIV, influenza and tumor-specific antigens, tetanus toxoid, diphtheria toxoid and other non-pathogenic mutants of these toxins, other toxins or non-pathogenic versions of these toxins that cause disease such as anthrax toxic complex, polysaccharides or peptide mimetics of polysaccharides from *Neisseria meningitiditis*, or *Streptococcus pneumoniae*. Preferably the antigen is selected from the group consisting of tetanus toxoid, diphtheria toxoid, and other non-pathogenic mutants of these toxins, other toxins or non-pathogenic versions thereof that cause disease such as anthrax toxic complex, antigens from *Bordatella pertussis*, rotavirus, hookworm, *M. tuberculosis*, Epstein-Barr virus, Hepatitis C virus, HIV, *Neisseria meningitiditis, Streptococcus pneumoniae*, polysaccharides or peptide mimetics of polysaccharides from *Neisseiria meningitiditis*, or *Streptococcus pneumoniae*, antigens from other blood-borne pathogens, tumor-specific antigens and antigens from viruses or bacteria against which vaccines are currently available. Most preferably the antigen is selected from the group consisting of tetanus toxoid, diphtheria toxoid and other mutants of these toxins, anthrax toxic complex, antigens from *Bordatella pertussis, M. tuberculosis*, HIV and antigens from viruses or bacteria against which vaccines are currently available. Particularly preferred is for the antigen to include one or more of tetanus toxoid, diphtheria toxoid and antigens from *Bordatella pertussis*. Although *Clostridium tetanii* does not generally invade its host via mucosal surfaces there are reported cases of tetanus entering the body through mucosal lesions. The immunogen composition may include two or more antigens. For example, one preferred immuogen composition includes tetanus toxoid (or a non-pathogenic mutant of tetanus toxoid) and diphtheria toxoid (or a non-pathogenic mutant of diphtheria toxoid).

The amount of antigen in the immunogen composition of the present invention varies depending on the nature and potency of the antigen. Typically, however, the amount of antigen present in the immunogen composition of the present invention is from about 0.000001% by weight of the immunogen composition to about 5% by weight of the immunogen composition, more typically from about 0.0001% by weight to about 5% by weight, and more typically from about 0.005% by weight to about 5% by weight. In one particular aspect of the present invention where the antigen is tetanus toxoid, the amount of tetanus toxoid present in the immunogen composition is typically from about 0.0001% by weight to about 0.05% by weight, preferably from about 0.0005% by weight to about 0.01% by weight, and more preferably from about 0.0005% by weight to about 0.003% by weight.

The immunogen composition of the present invention provides a delivery system that typically elicits stimulation of an immune response, which will typically include a systemic immune response when the immunogen composition is administered for systemic delivery of the antigen. Furthermore, the immunogen composition of the present invention provides a delivery system that elicits stimulation of a strong immune response, which will typically include both a strong systemic immune response and a strong mucosal immune response when the immunogen composition is administered for mucosal delivery of the antigen. Furthermore, the immunogen composition when administered for mucosal delivery can act as a boost to an existing immune response. Without being bound by any theory, it is believed that the immunogen composition of the present invention reduces or eliminates degradation of the antigen and allows for a relatively slow sustained administration of antigens to the host. The antigen is at least partially protected by the biocompatible polymer, thereby reducing susceptibility of the antigen to degradation and promoting increased effectiveness of the antigen. Also, it is believed that the immunogen composition of the present invention promotes improved bioadhesion onto and permeation into and across the mucous membrane, or mucosa, thus allowing the immunogen composition to exert its actions more efficaciously at the target site. This is particularly the case according to the invention when the immunogen composition includes an adjuvant and/or penetration enhancer that further enhances performance. Moreover, stabilizing agents may be incorporated into the immunogen composition to further reduce the susceptibility of the antigen to degradation, tending to further enhance the effectiveness of the immunogen composition to stimulate mucosal immunity and to also enhance stability of the antigen during storage and transportation of the composition.

The biocompatible polymer in the immunogen composition of the present invention typically is a reverse-thermal gelation polymer. The biocompatible polymer is selected and the immunogen composition is formulated with relative proportions of the liquid vehicle and the biocompatible polymer so that the immunogen composition exhibits reverse-thermal viscosity behavior across at least some temperature range, preferably a temperature range below 40° C., more preferably a temperature range below 37° C. and even more preferably a temperature range within a range of from 10° C. to 37° C. Typically, the immunogen composition exhibits reverse-thermal viscosity behavior over some temperature range within a range of 1° C. to 20° C. Due to the reverse thermal viscosity behavior of the immunogen composition, the immunogen composition can be administered to the host at a cooler temperature where the composition has a lower viscosity, with the viscosity of the composition then increasing in the host following administration, whereby the mobility of the composition is severely reduced within the host following administration. When the immunogen composition has a reverse thermal gelation property, then the immunogen composition will exist in the form of a flowable medium at least at a first temperature and in the form of a gel at least at a second temperature that is higher than the first temperature. Preferably both the first and second temperatures are below 40° C., and more preferably the second temperature is no higher than 37° C. A preferred situation is when the first temperature is in a range of 1° C. to 20° C. and the second temperature is in a range of 25 ° C. to 37° C.

In a particularly preferred embodiment, the immunogen composition is formulated with relative proportions of liquid vehicle and biocompatible polymer so that the immunogen composition has a reverse-thermal gelation property, preferably with a reverse-thermal liquid-gel transition temperature so that when the immunogen composition is administered to a host, the biocompatible polymer and also the immunogen composition becomes a gel or gelatinous in vivo, thus reducing or eliminating degradation of the antigen and/or achieving the ability for slow release, i.e., sustained administration, of the antigen for a time period of many hours, days, weeks or even months, depending upon the specific application.

Any biocompatible polymer may be used that, as formulated in the immunogen composition, is capable of interacting with the liquid vehicle to impart the desired reverse-thermal viscosity behavior to the immunogen composition. Non-limiting examples of some reverse-thermal gelation polymers useful for preparing the immunogen composition include certain polyethers (preferably polyoxyalkylene block copolymers with more preferred polyoxyalkylene block copolymers including polyoxyethylene-polyoxypropylene block copolymers referred to herein as POE-POP block copolymers, such as Pluronic™ F68, Pluronic™ F127, Pluronic™ L121, and Pluronic™ L101, and Tetronic™ T1501); certain cellulosic polymers, such as ethylhydroxyethyl cellulose; and certain poly (ether-ester) block copolymers (such as those disclosed in U.S. Pat. No. 5,702,717). Pluronic™ and Tetronic™ are trademarks of BASF Corporation. Furthermore, more than one of these and/or other biocompatible polymers may be included in the immunogen composition to provide the desired characteristics and other polymers and/or other additives may also be included in the immunogen composition to the extent the inclusion is not inconsistent with performance requirements of the immunogen composition. Furthermore, these polymers may be mixed with other polymers or other additives, such as sugars, to vary the transition temperature, typically in aqueous solutions, at which reverse-thermal gelation occurs.

Polyoxyalkylene block copolymers are particularly preferred to use as the biocompatible reverse-thermal gelation polymer. A polyoxyalkylene block copolymer is a polymer including at least one block (i.e. polymer segment) of a first polyoxyalkylene and at least one block of a second polyoxyalkylene, although other blocks may be present as well. POE-POP block copolymers are one class of preferred polyoxyalkylene block copolymers for use as the biocompatible reverse-thermal gelation polymer in the immunogen composition. POE-POP block copolymers include at least one block of a polyoxyethylene and at least one block of a polyoxypropylene, although other blocks may be present as well. The polyoxyethylene block may be represented by the formula $(C_2H_4O)_b$ when b is an integer. The polyoxypropylene block may be represented by the formula $(C_3H_6O)_a$ when a is an integer. The polyoxypropylene block could be for example $(CH_2CH_2CH_2O)_a$, or could be

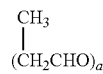

Several POE-POP block copolymers are known to exhibit reverse-thermal gelation properties, and these polymers are particularly preferred for imparting reverse-thermal gelation properties to the immunogen composition of the present invention. Examples of POE-POP block copolymers include Pluronic™ F68, Pluronic™ F127, Pluronic™ L121, Pluronic™ L101, and Tetronic™ T1501. Tetronic™ T1501 is one example of a POE-POP block copolymer having at least one polymer segment in addition to the polyoxyethylene and polyoxypropylene segments. Tetronic™ T1501 is reported by BASF Corporation to be a block copolymer including polymer segments, or blocks, of ethylene oxide, propylene oxide and ethylene diamine.

As will be appreciated, any number of biocompatible polymers may now or hereafter exist that are capable of imparting the desired reverse-thermal viscosity behavior and/or reverse-thermal gelation properties for the immunogen composition of the present invention, and such polymers are specifically intended to be within the scope of the present invention when incorporated into the immunogen composition.

Some preferred POE-POP block copolymers have the formula:

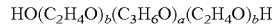

which, in the preferred embodiment, has the property of being liquid at ambient or lower temperatures and existing as a semi-solid gel at mammalian body temperatures wherein a and b are integers in the range of 15 to 80 and 50 to 150, respectively. A particularly preferred POE-POP block copolymer for use with the present invention has the following formula:

wherein a and b are integers such that the hydrophobe base represented by $(CH_2(CH_3)CHO)_a$ has a molecular weight of about 4,000, as determined by hydroxyl number; the polyoxyethylene chain constituting about 70 percent of the total number of monomeric units in the molecule and where the copolymer has an average molecular weight of about 12,600. Pluronic™ F-127, also known as Poloxamer 407, is such a material. In addition, a structurally similar Pluronic™ F-68 may also be used.

The procedures used to prepare aqueous solutions which form gels of polyoxyalkylene block copolymer are well known and are disclosed in U.S. Pat. No. 5,861,174, which is incorporated herein by reference in its entirety. The relative proportions of the liquid vehicle and the biocompatible polymer, as formulated in the immunogen composition, should be selected so that the resulting immunogen composition has reverse-thermal gelation properties with a reverse-thermal liquid-gel transition temperature of less than about 37° C., preferably between about 10° C. and 37 ° C., and more preferably between about 20° C. to about 37° C. The amount of biocompatible polymer in the immunogen composition of the present invention is typically from about 1% by weight to about 50% by weight of the immunogen composition, preferably from about 8% by weight to about 33% by weight, and more preferably from about 13% by weight to about 25% by weight.

In one preferred embodiment of the present invention, the immunogen composition includes an additive that is an adjuvant and/or a penetration enhancer. In some instances a single compound may act both as a penetration enhancer and an adjuvant when incorporated into the immunogen composition. This is the case, for example, with chitosan and other chitosan materials, which are especially preferred additives for use in the immunogen composition. Chitosan is a polysaccharide derived from deacetylation of chitosan. As used herein, "chitosan materials" include chitosan, derivatives of chitosan and other derivatives originating from chitin that provide adjuvant and/or penetration enhancer properties similar to chitosan. The use of chitosan material as a combined penetration enhancer/adjuvant is especially preferred when the immunogen composition is administered mucosally.

Non-limiting examples of penetration enhancers include various molecular weight chitosan materials, such as chitosan and N,O-carboxymethyl chitosan; poly-L-arginines; fatty acids, such as lauric acid; bile salts such as deoxycholate, glycolate, cholate, taurocholate, taurodeoxycholate, and glycodeoxycholate; salts of fusidic acid such as taurodihydrofusidate; polyoxyethylenesorbitan such as Tween™ 20 and Tween™ 80; sodium lauryl sulfate; polyoxyethylene-9-lauryl ether (Laureth™-9); EDTA; citric acid; salicylates; caprylic/capric glycerides; sodium caprylate; sodium caprate; sodium laurate; sodium glycyrrhetinate; dipotassium glycyrrhizinate; glycyrrhetinic acid hydrogen succinate, disodium salt (Carbenoxolone™); acylcarnitines such as palmitoylcarnitine; cyclodextrin; and phospholipids, such as lysophosphatidylcholine. Preferably, the penetration enhancer is selected from the group consisting of chitosan materials, and fatty acids, polyethylene sorbitol and caprylic/capric glycerides. More preferably, the penetration enhancer is selected from the group consisting of chitosan materials, fatty acids and caprylic/capric glycerides. Particularly preferred as the penetration enhancers are the chitosan materials. As used herein, a "penetration enhancer" is any substance or material that, when added to a formulation including an active agent, such as the antigen in the immunogen composition, enables or enhances permeation of the active agent across biological membranes thereby increasing absorption and systemic bioavailability of the active agent. In the case of a formulation with an active agent delivered by a mucosal route, the penetration enhancer enables or enhances permeation of the active agent across the mucosal epithelium where the active agent is to be delivered.

Non-limiting examples of adjuvants for use in the immunogen composition include those materials that exhibit adjuvantic properties in mucosal tissues including chitosan materials, bacterially derived products such as monophosphoryl lipid A, CpG motifs, detoxified mutants of CT and ET, and outer membrane proteins of *Neisseria meningitidis* serogroup b. Other non-limiting examples of adjuvants for use in the immunogen composition include those materials that exhibit adjuvantic properties in non-mucosal tissues including dimethyl dioctadecyl ammonium bromide (DDA), CpG motifs, cytokines such as IL-12 and IL-6, as well as chitosan materials.

When present, the amount of penetration enhancer and/or adjuvant in the immunogen composition of the present invention generally varies depending on the particular additive(s) used. However, a typical amount of penetration enhancer present in the immunogen composition of the present invention is from about 0.001% by weight to about 10% by weight of the immunogen composition, preferably from about 0.01% by weight to about 5% by weight, and more preferably from about 0.01% by weight to about 1.0% by weight. In one particular aspect of the present invention when a chitosan materials is used as a penetration enhancer and/or an adjuvant, the amount of the chitosan or chitosan material present in the immunogen composition is typically from about 0.01% by weight to about 10% by weight of the immunogen composition, preferably from about 0.1% by weight to about 1% by weight, and more preferably from about 0.1% by weight to about 0.5% by weight. In one preferred composition, the immunogen composition comprises from 60 weight percent to 85 weight percent of the liquid vehicle, from 0.0001 weight percent to 5 weight percent of the antigen and from 0.01 weight percent to 1.0 weight percent of at least one of the adjuvant an/or penetration enhancer additive.

The immunogen composition of the present invention can also include other additives besides adjuvant and/or penetration enhancer. For example, the immunogen composition can include polymer or protein stabilizers such as trehalose, sucrose, glycine, mannitol, albumin, and glycerol.

Any suitable liquid vehicle can be used that is capable of interacting with the biocompatible polymer to impact the desired reverse thermal viscosity behavior. Preferably the biocompatible polymer, and also preferably the antigen, is soluble in the liquid vehicle at least at a temperature at which the immunogen composition is in the form of a flowable medium suitable for administration. The adjuvant and/or penetration enhancer are also preferably soluble in the liquid vehicle in the flowable medium form suitable for administration. The immunogen composition is typically prepared in water, a saline solution or other aqueous liquid as the liquid vehicle, although any solvent, including mixtures of multiple solvent liquids, can be used, depending upon the specific circumstances of the application. Under ordinary conditions of storage and use, the immunogen composition may also contain a preservative to prevent the growth of microorganisms, Preferably, the immunogen composition is sterile, and is fluid, i.e., in the form of a flowable liquid or suspension, when administered to accommodate easy syringability and/or nebulization. The immunogen composition should preferably be stable under the conditions of manufacture and storage and should also preferably be preserved against the contaminating action of microorganisms such as bacteria and fungi. The liquid vehicle can be a solvent or dispersion medium containing, for example, water, ethanol, polyol (e.g., glycerol, propylene glycol, and liquid polyethylene glycol, and the like), and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars, phosphate buffers, sodium chloride, or mixtures thereof.

In another embodiment, antigen-stabilizing solutes, typically protein-stabilizing solutes, are incorporated into the immunogen composition. The use of protein-stabilizing solutes, such as sucrose, not only aids in protecting and stabilizing the antigen (especially when the antigen is a protein), but also permits manipulation of the reverse-thermal gelation properties of the composition. For example, addition of certain protein-stabilizing solvents permits the composition to exhibit desired reverse-thermal gelation behavior at lower polymer concentration and/or at an altered reverse-thermal gelation temperature than when the protein-stabilizing is not used, especially when using the preferred polyalkoxyalkylene block copolymers. Thus, the working range of polymer concentration can be widened and the transition temperature modified. It is known that in some cases a gel will not form when the concentration of polyoxyethylene-polyoxypropylene block copolymer in water or dilute buffer is outside a particular range, e.g., equal to or less than 15% percent by weight for some polymers. However, by introducing protein-stabilizing solutes to the immunogen composition of the present invention, the transition temperature may be manipulated, while also lowering the concentration of polyoxyethylene-polyoxypropylene block copolymer that is necessary to form a gel. In this regard, preferred protein-stability solvents are sugars, such as, for example, sucrose.

The immunogen composition of the present invention is particularly effective for stimulating or upregulating a antibody response to a level greater than that seen with conventional formulations and administration schedules. More preferably the immunogen composition of the present invention, upon administration, stimulates a systemic immune response that protects the host from at least one pathogen. Most preferably the immunogen composition of the present invention, upon administration, stimulates a systemic and mucosal immune response that protects the host from at least one pathogen. As will be appreciated a immune response involves generation of one or more antibody classes, such as IgM, IgG and/or IgA, and typically for mucosal responses at least IgA.

In one aspect, the invention provides a method for delivery of an antigen to a host to stimulate an immune response in the host. The method involves administering the immunogen composition of the present invention to the host, which is usually accomplished by introducing the immunogen composition into the host in a manner to stimulate a desired immune response. The immunogen composition can be introduced into the host by any suitable technique. For example, in one embodiment, the immunogen composition is introduced into the host by injection, such as, for example, subcutenously, intramuscularly, or intraperitoneally. The injection may be accomplished using any suitable injection device, such as, for example, a syringe.

In another embodiment, the immunogen composition is introduced into the host for delivery of the antigen via a mucosal route. In this embodiment, the immunogen composition is introduced into the host in a manner so that at least a portion, and preferably most or all, of the administered immunogen composition contacts a mucosal surface within the host. At least a portion, and more preferably at least a significant portion, of the immunogen composition adheres to the mucosal surface, thereby retaining the antigen, and also any adjuvant and/or penetration enhancer in the vicinity of the mucosal surface to promote uptake of the antigen across the mucosal surface.

Whether administered by injection or mucosally, the immunogen composition should be in the form of a flowable medium immediately prior to introduction of the immunogen composition into the host. This will typically require that the immunogen composition be at a temperature that is lower than the physiologic temperature of the host. In the case of a human host, having a physiologic temperature of 37° C., the temperature of the immunogen composition immediately prior to administration will frequently be 25° C. or less and more often 20° C. or less. In most instances, the temperature of the immunogen composition immediately prior to introduction into the host will be in a range of from about 1°C. to about 20°C.

After introduction into the host, the immunogen composition is warmed to the physiologic temperature of the host and, due to the reverse-thermal viscosity behavior of the immunogen composition, the viscosity of the immunogen composition increases inside the host as the temperature of the immunogen composition increases. When the immunogen composition has a reverse-thermal liquid-gel transition temperature between the temperature of administration and the physiologic temperature of the host, then the immunogen composition will convert from the form of a flowable medium to a gel form inside the host following administration. Thus the reverse-thermal gelation property of the immunogen composition is advantageous to permit easy administration of the immunogen composition to the host as a flowable medium and the viscosity then advantageously increases after administration at least partially to immobilize the immunogen composition at the location where delivery of the antigen is desired. This is particularly advantageous when the antigen is to be delivered via a mucosal route, because the high viscosity/gel nature of the immunogen composition following administration causes the immunogen composition to readily adhere to mucosal surfaces, so that the immunogen composition, including the antigen and any additives are retained in the vicinity of the mucosal surface to facilitate delivery of the antigen across the mucosal surface.

When the antigen is delivered via a mucosal route, the immunogen composition may be directed to contact any desired mucosal surface to permit delivery of at least a portion of the antigen across the mucosal epithelium at that location to elicit an immune response. The mucosal surface may, for example, be a sublingual, buccal, oral, intranasal, gastrointestinal, pulmonary, vaginal, rectal, aural, or ocular mucosal surface. For many of these mucosal delivery applications, such as for oral, intranasal, pulmonary and sublingual, it is preferred that the immunogen composition is introduced into the host in the form of a mist containing a dispersion of fine droplets of the immunogen composition. Typically, the mist will be produced by a nebulizer actuatable to produce the mist. For example, one preferred mucosal delivery route is intranasal and the mist could be generated by a nasal nebulizer. When generated by the nasal nebulizer, the spray is directed into the nasal cavity to introduce the immunogen composition into the host to contact a mucosal surface within the nasal cavity.

Whether the immunogen composition is delivered by injection or mucosally, the biocompatible polymer, and preferably also the antigen and any adjuvant and/or penetration enhancer are dissolved in the liquid vehicle. As the composition gels within the host, at least a portion of the polymer, and potentially also some or all of the antigen and other additives come out of solution.

In another aspect of the invention, a method is provided for packaging and storing the immunogen composition. According to this aspect of the invention, the immunogen composition is placed in a container when the composition is in the form of a flowable medium. The temperature of the composition is then raised so that the immunogen composition converts to a gel form within the container for storage. Following storage in the gel form, the immunogen composition in the container can be converted back to a flowable medium for administration to the host at the appropriate time by lowering the temperature of the composition in the container. In this way, the immunogen composition is easy to handle during manufacturing and packaging operations, but can be stored in the highly stable form of a gel. Furthermore, the composition can be converted back to a flowable medium for ease of administration.

It is not, however, required that the immunogen composition be stored at a temperature below the transition temperature. The immunogen composition may be stored in a gel form above the transition temperature and then cooled to below the transition temperature prior to administration. This ability to store the antigen in a gel form of the immunogen composition prior to use is a distinct advantage with the present invention. Alternatively, the immunogen composition could be stored in the form of a flowable medium at a temperature below the reverse-thermal liquid-gel transition temperature, but such a fluid form is often not as convenient for handling and storage as a gel form. In either case, the immunogen composition is advantageous for storing the antigen in a highly protective environment prior to use.

In another aspect, a method for making the immunogen composition is provided, comprising dissolving the biocompatible polymer in a liquid vehicle and suspending or codissolving the antigen in the liquid vehicle. Preferably, both the antigen and the biocompatible polymers are dissolved in the liquid vehicle.

The present invention has been described primarily with reference to the immunogen composition. The principles discussed with respect to formulation, manufacture, storage, and administration of the immunogen composition apply equally to the delivery of other drugs. In that regard, the aspects of the present invention as described above can be applied to formulate, prepare, restore, and administer a delivery vehicle composition for delivering any drug in a therapeutically effective amount for treatment of at least one condition in the host. The delivery vehicle includes at least the drug, the biocompatible polymer and the liquid vehicle, with the proportions of the liquid vehicle and the biocompatible polymer being such that the delivery vehicle composition exhibits reverse-thermal viscosity behavior, and preferably, a reverse-thermal gelation property, as discussed above specifically with respect to the immunogen composition. In a preferred embodiment, the delivery vehicle composition includes as an additive at least one of an adjuvant and a penetration enhancer for the drug to be delivered.

Throughout this specification, the entire contents of any and all references to publicly available documents, including any U.S. patents, are specifically incorporated by reference.

The following examples are given to illustrate the present invention. It should be understood, however, that the invention is not to be limited to the specific conditions or details described in these examples.

EXAMPLES

Example 1

Preparation of Tetanus Toxoid Formulations. Tetanus Toxoid (TT) solution was obtained (Accurate Chemical, Accurate & Scientific Corp., Westerbury, N.Y.) containing 961 LfTT per mL of solution and 1884 LfTT per mg of protein nitrogen. Pluronic® F127 (BASF, Washington, N.J.) stock solution was prepared at 30 or 34%(w/w) by dissolving the polymer in ice-cold phosphate buffer solution (PBS) with complete dissolution achieved by storing overnight at 4° C. Chitosan (Sigma-Aldrich, St. Louis, Mo., medium molecular weight chitosan) stock solution was prepared at 3% (w/w) in a 0.9% (w/v) saline solution containing 0.1% (v/v) acetic acid and heated overnight at 37° C. to dissolve the chitosan. The stock solutions were then mixed together to prepare formulations containing various combinations of 200 Lf/mL TT, 0.5% (w/w) chitosan, and 16.25% (w/w) Pluronic® F127. These formulations were used to administer a dose of 1.5 Lf of TT per mouse. If the antigen formulation is to be administered intranasally the application is 7.5 µL/mouse.

Immunization in mice. Balb/c mice, 6-8 weeks of age (Taconic Farms Incorp., Germantown, N.Y.), were used for the study. Intranasal immunization was performed under anesthesia with Ketamine/Xylazine 80mg/16mg/kg.

Nasal and pulmonary IgA anti-TT antibody assays. Post mortem lung washes were obtained by gently injecting 300 µL of cold solution consisting of 5mM EDTA, 0.5 % gelatin, 0.05% Tween™ 80 in PBS into the lungs through a syringe connected to the trachea. The lavage fluid was aspirated and the procedure was repeated once (total of 600 µL is collected). Nasal washes were performed by injection of 300 µL cold solution as above retrograde via the trachea into the nasopharynx. The lavage fluid was collected at the nostrils. The IgA anti-TT antibody response was determined by ELISA. Wells of 96 well Nunc Maxisorb microtiter plates (Nunc, Gaithersburg, MD) were coated with 100 µL of 1 µg/ml TT in PBS overnight at 4° C. Plates were washed with PBS/0.05% Tween™ 20 and blocked with 200 µl of 1 % bovine serum albumin (BSA) (Fisher Scientific, Pittsburgh, Pa.) in ultra-pure water for 2 hrs at 37° C. Serum was serially diluted in PBS with 0.1% BSA/0.05% Tween™ 20 and 50 µl added per well. Following incubation overnight at 4° C., plates were washed and the secondary antibody consisting of horse radish peroxidase-conjugated goat anti-mouse IgA antibody (Southern Biotechnology Associates, Inc., Birmingham, Ala.) was added to wells at a dilution of 1:2000 in PBS with 0.1% BSA and 0.05% Tween™ 20. The plates were incubated for 2 hrs at 37° C. and antibody binding was detected with substrate buffer containing 0.02% o-phenylenediamine (Sigma-Aldrich). Absorbance was read at 450 nm with an EIA reader (Bio-Tek Instruments, Burlington, Vt.).

IgA anti-TT antibody response in lung and nasal washes after i.n. boost. Mice were primed intraperitoneally (i.p.) with 1.5 LfTT in PBS. Four weeks later they were boosted intranasally (i.n.) with either 1.5 LfTT formulated in F127/chitosan or a formulation of F127/ chitosan alone (vehicle control) or boosted i.p. with 1.5 LfTT in PBS (control). The secretory IgA anti-TT antibody titers in lung washes and nasal secretions were measured at week 10 (6 weeks after boosting). FIG. 1 is a bar graph showing average reciprocal titer IgA levels in lung and nasal washes for test conditions summarized in Table 1.

TABLE 1

| Group | TT Prime Formulation and Administration Route, Day 0 | TT Boost Form./Admin. Week 4 |
|---|---|---|
| 1 | 1.5 LfTT/PBS, i.p. | 1.5 LfTT/F127/Chitosan, i.n. |
| 2 | 1.5 LfTT/PBS, i.p. | 1.5 LfTT/PBS (Control), i.p. |
| 3 | 1.5 LfTT/PBS, i.p. | F127/Chitosan (Vehicle Control), i.n. |

As shown in FIG. 1, the secretory IgA anti-TT antibody concentrations in the i.n. boosted F127/chitosan group were significantly higher in both lung and nasal washes (p=0.014) as compared to levels in animals boosted i.p. with TT in PBS. These data indicate that i.n. booster immunization with TT/F127/chitosan significantly increased IgA production at the lung and nasal mucosal surfaces compared to systemic (i.p.) booster immunization.

Example 2

The methods used in this example were the same as those used in Example 1, except as specifically noted.

IgA anti-JT antibody responses in lung and nasal washes after i.n. immunization and boost. Balb/c mice were immunized i.n. at week 0 and boosted i.n. at weeks 1 and 3 with 1.5 LfTT in PBS (controls) or 1.5 LfTT formulated with F127/chitosan. IgA anti-TT antibody levels were measured by ELISA, as described for Example 1, at 4 weeks (i.e. one week after the final boost injection).

Figure 2:
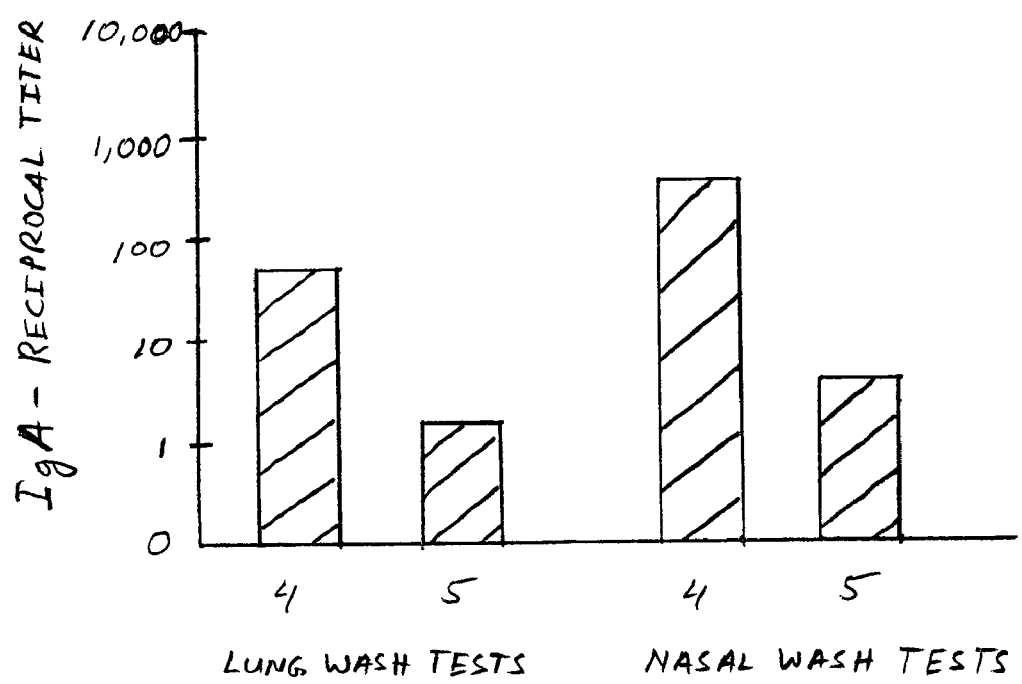
FIG. 2 is a graph of IgA anti-TT antibody response measured in the lung and nasal washes of inbred mice immunized i.n. three times with 1.5 LfTT in either PBS or F127/chitosan.

FIG. 2 is a bar graph showing average reciprocal titer IgA anti-TT antibody levels in lung and nasal washes for test conditions using the formulations summarized in Table 2.

TABLE 2

| Group | TT Immunization Formulation and Administration Route at Week 0 | TT Boost Form./Admin. Week 1 | TT Boost Form./Admin. Week 3 |
|---|---|---|---|
| 4 | 1.5 LfTT/F127/ Chitosan, i.n. | 1.5 Lf. TT/F127/Chitosan, i.n. | 1.5 Lf. TT/F127/Chitosan, i.n. |
| 5 | 1.5 LfTT/PBS (Control), i.n. | 1.5 LfTT/PBS (Control), i.n. | 1.5 LfTT/PBS (Control), i.n. |

As shown in FIG. 2, the IgA anti-TT antibody responses in the lung washes of mice immunized and boosted i.n. with TT in F127/chitosan were significantly enhanced (approximately 30-fold) as compared to the mice treated with TT in PBS (p=0.0006). Also as shown in FIG. 2, the secretory IgA response in the nasal washes was also dramatically enhanced in the TT/F127/chitosan treated group and was approximately 90-fold higher than that of the animals receiving TT in PBS (p=0.004). The results of these studies indicate that i.n.

immunizations with TT in F127/chitosan induced a significant IgA anti-TT response, in contrast to i.n. immunization with TT in PBS.

Example 3

The preparation of tetanus toxoid and immunization of mice used in this example were the same as those used in Example 1, except as specifically noted.

Measurement of IgG antibody responses in sera. The serum antibody response to TT was measured by ELISA on a weekly basis. Sera was obtained by tail vein bleeding and stored at −20° C. until assay. Wells of 96 well Maxisorb microtiter plates were coated with 100 μl of 1 μg/ml TT in PBS overnight at 4° C. Plates were washed with PBS/0.05% Tween 20 and blocked with 200 μl of 1 % bovine serum albumin (BSA) (Fisher Scientific) in ultrapure water for 2 hr at 37° C. Serum samples were serially diluted in PBS with 0.1% BSA/0.05% Tween 20, 50 gl of sample was added per well. Following incubation overnight at 4° C., plates were washed and horseradish peroxidase-labeled anti-mouse IgG γchain-specific antibody conjugate (Southern Biotechnology Associates, Inc.) was added diluted to 1:3000 in PBS with 0.1% BSA and 0.05% Tween 20. The plates were incubated for 2 hr at 37° C. and antibody binding was detected with substrate buffer containing 0.02% o-phenylenediamine (Sigma-Aldrich). Absorbance was read at 450 nm with an EIA reader (Bio-Tek Instruments). Immunoglobulin titers are calculated as follows. For serum antibodies the titer is defined as the reciprocal of the dilution that would yield an optical density of 0.5. Geometric mean titers, averages and standard deviations are calculated using Microsoft Excel. Mann Whitney U is used to calculate statistical difference between titers of groups, values are significant when $P<0.05$.

Figure 3:
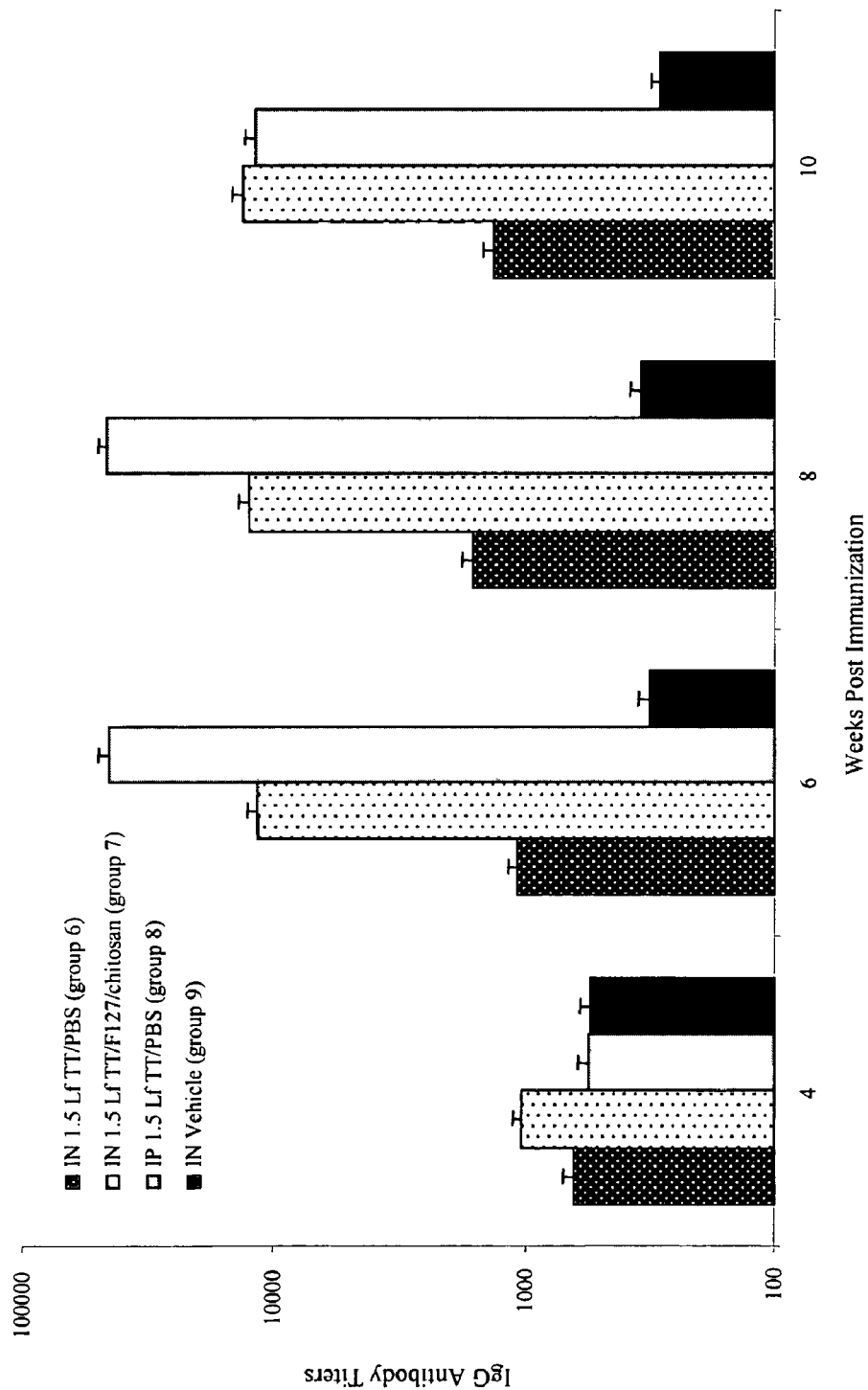
FIG. 3 is a graph of the IgG anti-TT antibody response over time in sera of inbred mice immunized i.p. at day 0 with 1.5 LfTT in PBS and subsequently boosted i.n. four weeks later with 1.5 LfTT in either PBS or F127/chitosan.

IgG anti-TT antibody response in sera after i.n. boost. Mice were primed i.p. with 1.5 LfTT in PBS at week 0 and boosted i.n. at week 4 with 1.5 LfTT in PBS or in F127/chitosan. The serum IgG anti-TT antibody response was analyzed on a biweekly basis for 10 weeks. In addition a group of mice was both primed and boosted i.p. with 1.5 LfTT in PBS. The results of the IgG anti-TT response from 4 weeks (pre-boost) to 10 weeks (6 weeks post-boost) is shown in FIG. 3. The IgM anti-TT antibody response is not shown as it was present in all groups, in equal amounts and comprises <10% of the immune response. The IgG anti-TT response of the mice boosted i.n. with TT in PBS is not significantly statistically different from the negative controls, i.e. mice boosted i.n. with vehicle. In contrast, mice boosted i.n. with TT in F127/chitosan manifested an IgG anti-TT antibody response significantly higher than all negative controls and the animals boosted i.n. with TT in PBS. At 10 weeks, there was no significant difference between the TT F127/chitosan i.n. group and the animals immunized and boosted systemically with TT.

TABLE 3

| Group | TT Prime Formulation and Administration Route, Week 0 | TT Boost Form./Admin. Week 4 |
| --- | --- | --- |
| 6 | 1.5 LfTT/PBS, i.p. | 1.5 LfTT/PBS (Control), i.n. |
| 7 | 1.5 LfTT/PBS, i.p. | 1.5 LfTT/F127/Chitosan, i.n. |
| 8 | 1.5 LfTT/PBS, i.p. | 1.5 LfTT/PBS (Control), i.p. |
| 9 | 1.5 LfTT/PBS, i.p. | 0.0 LfF127/Chitosan (Vehicle Control), i.n. |

Example 4

The methods used in this example were the same as those described in Example 3, except as noted.

Figure 4:
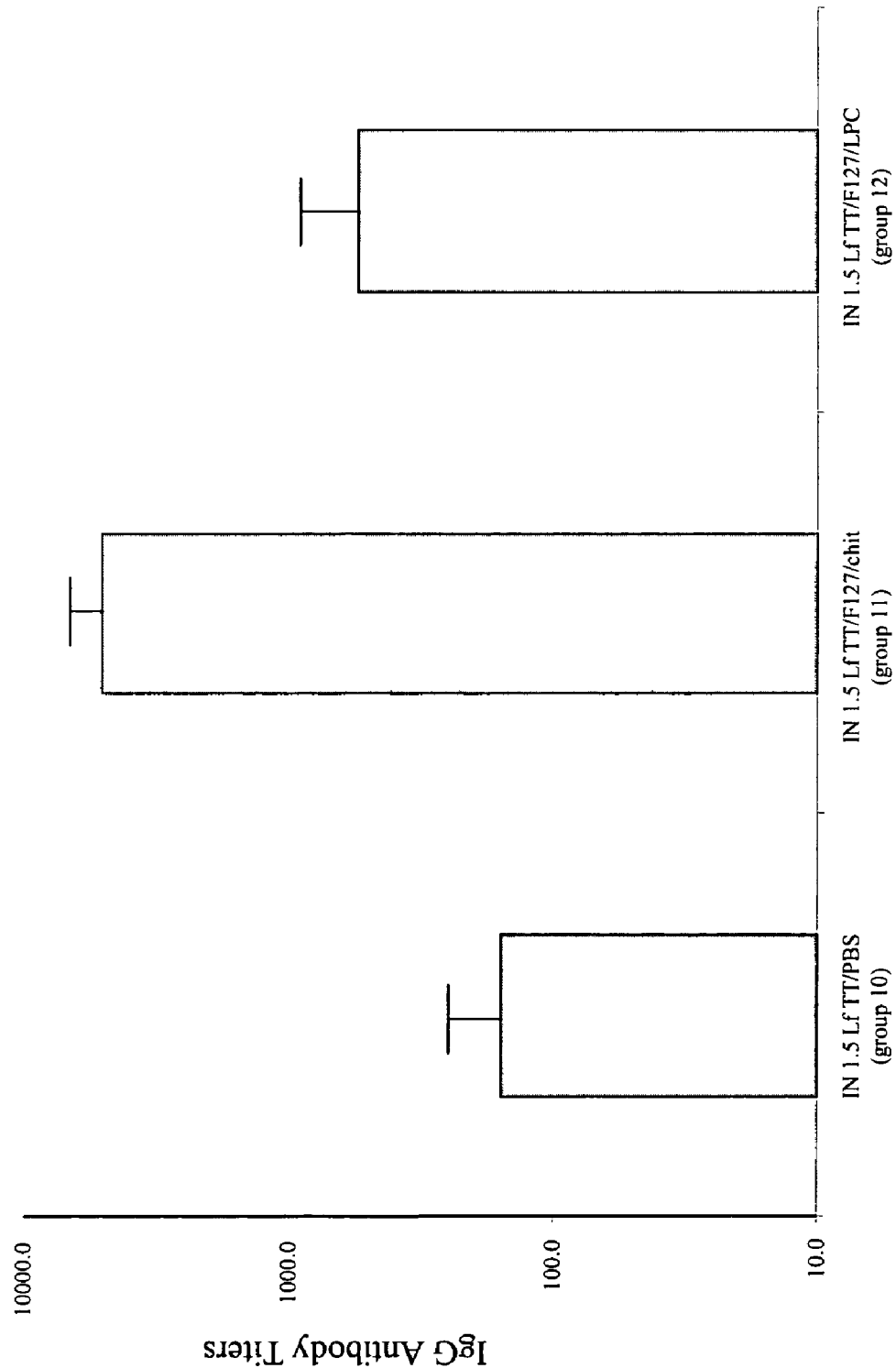
FIG. 4 is a graph of the IgG anti-TT antibody response over time in sera of inbred mice after i.n. immunization at week 0 followed by i.n. booster immunization at weeks 1 and 3 with TT in various formulations.

IgG anti-TT antibody response in sera to intranasal immunization and boost. The IgG antibody response to i.n. immunization and booster was assessed by treating groups of Balb/c mice via i.n. immunization at week 0 followed by i.n. booster immunization at weeks 1 and 3. The IgG anti-TT responses of mice immunized and boosted i.n. with TT in PBS, TT in F127/chitosan and TT in F127/LPC were compared. The results of these studies are shown in FIG. 4 and indicate that the animals treated i.n. with TT in PBS failed to generate a significant anti-TT immune response, with a geometric mean titer of 159.6. The group immunized with TT in F127/LPC had a measurable anti-TT IgG response with a geometric mean titer of 544. The group immunized with TT in F127/chitosan clearly demonstrated a significant systemic anti-TT IgG response with a geometric mean titer >5000. These studies indicate that intranasal immunization with TT in F127/chitosan induces a significant systemic IgG anti-TT antibody response.

TABLE 4

| Group | TT Immunization Formulation and Administration Route at Week 0 | TT Boost Form./Admin. Week 1 | TT Boost Form./Admin. Week 3 |
| --- | --- | --- | --- |
| 10 | 1.5 LfTT/PBS (Control), i.n. | 1.5 LfTT/PBS (Control), i.n. | 1.5 LfTT/PBS (Control), i.n. |
| 11 | 1.5 LfTT/F127/Chitosan, i.n. | 1.5 LfTT/F127/Chitosan, i.n. | 1.5 LfTT/F127/Chitosan, i.n. |
| 12 | 1.5 LfTT/F127/LPC, i.n. | 1.5 LfTT/F127/LPC, i.n. | 1.5 LfTT/F127/LPC, i.n. |

Example 5

The methods used in this example were the same as those described in Example 3, except as noted.

Figure 5:
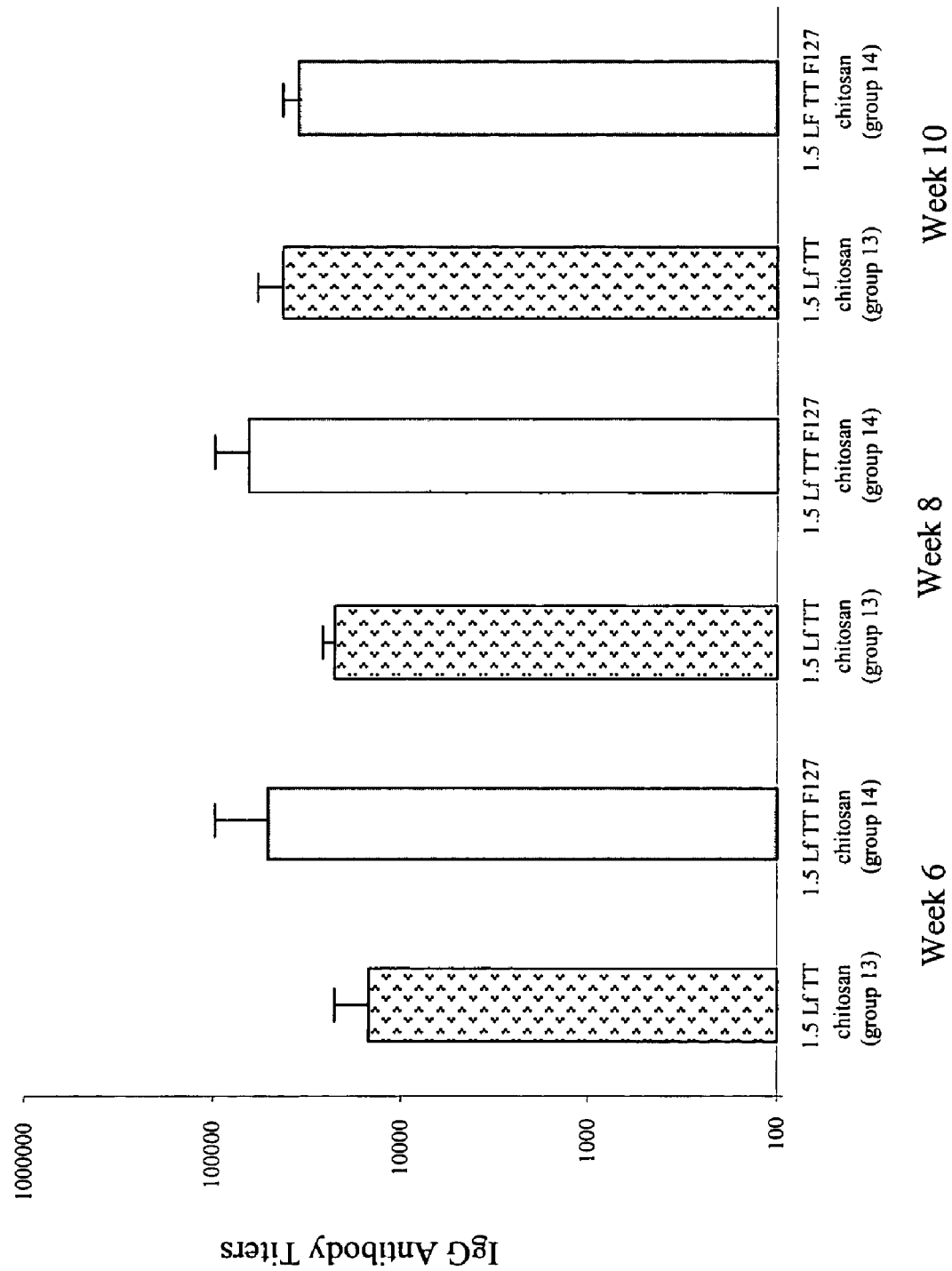
FIG. 5 is a graph of the IgG anti-TT antibody response over time in sera of inbred mice immunized i.p. at day 0 with 1.5 LfTT in PBS and subsequently boosted i.n. four weeks later with 1.5 LfTT in either F127/chitosan or chitosan alone.

Comparative analysis of TT in F127/chitosan vs. TT in chitosan. To define the role of F127 in the formulations, Balb/c mice were primed i.p. with 1.5 LfTT in PBS and subsequently boosted i.n. four weeks later with 1.5 LfTT in F127/chitosan or TT in chitosan without F127. The results of these experiments are shown in FIG. 5 and indicate that the immune response to TT/chitosan was significantly lower than the immune response to TT in F127/chitosan over the first two weeks following boost (p=0.023)

TABLE 5

| Group | TT Prime Formulation and Administration Route, Week 0 | TT Boost Form./Admin. Week 4 |
| --- | --- | --- |
| 13 | 1.5 LfTT/PBS, i.p. | 1.5 LfTT/Chitosan, i.n. |
| 14 | 1.5 LfTT/PBS, i.p. | 1.5 LfTT/F127/Chitosan, i.n |

Example 6

The methods used in this example were the same as those described in Example 3, except as noted.

Figure 6:
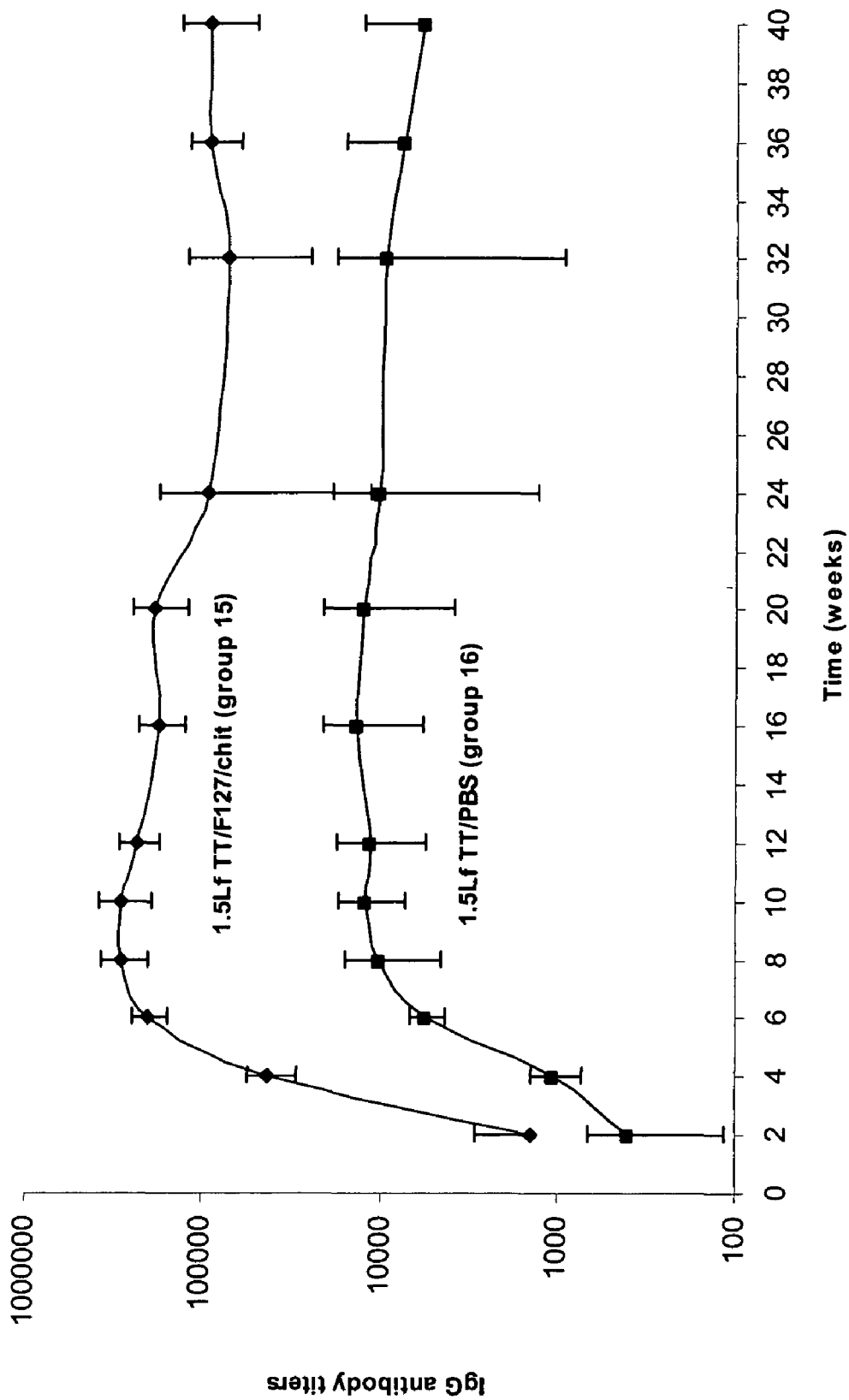
FIG. 6 is a graph of the IgG anti-TT antibody response over time in sera of inbred mice immunized once subcutaneously (s.c.) with 1.5 LfTT in various formulations.

Subcutaneous (s.c.) immunization elicits a long-lasting JgG antibody response. Groups of Balb/c female mice (n=8) were immunized once s.c. with 1.5 LfTT in F127/chitosan or in PBS. Methods for preparation of the formulations were similar to those described in Example 1, except that the final concentration of TT in the formulation was 15 Lf/ml and 0.1 ml per mouse was injected. Serum samples were collected at various time points and analyzed for the presence of IgG anti-TT antibodies by ELISA as described in Example 3. As shown in FIG. 6, the combination of TT/F127/chitosan elicited a very long-lasting antibody response with titers persisting at levels above 90,000 for at least 10 months.

TABLE 6

| Group | Single Injection Formulation and Administration Route |
|---|---|
| 15 | 1.5 LfTT/127/Chitosan, s.c. |
| 16 | 1.5 LfTT/PBS (Control), s.c. |

Example 7

The methods used in this example were the same as those described in Example 6, except as noted.

Figure 7:
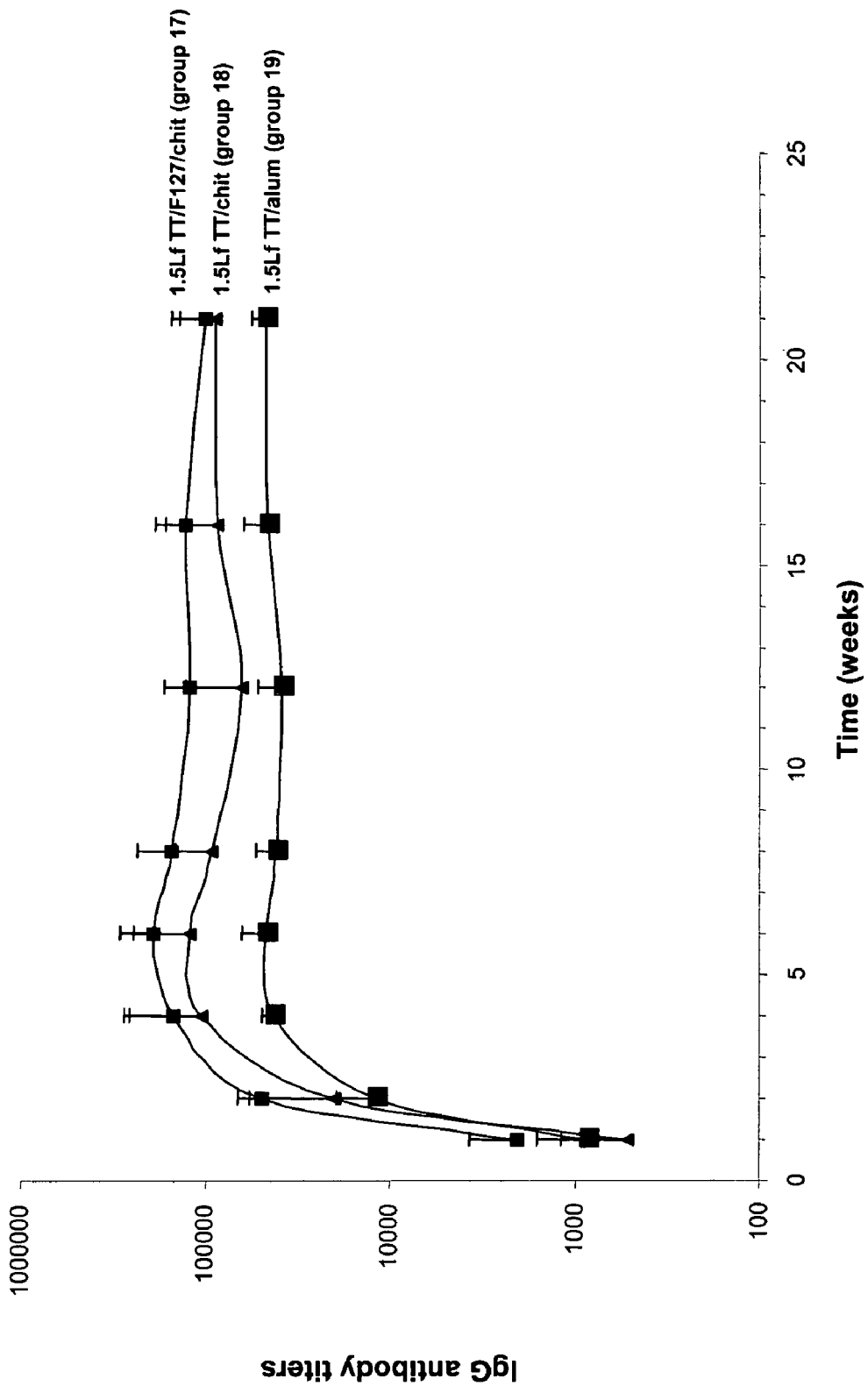
FIG. 7 is a graph of IgG anti-TT antibody response in outbred mice over time after a single s.c. immunization with TT in F127/chitosan or mixed with chitosan only or after three s.c. immunizations with TT adsorbed to aluminum salts (alum).
Figure 8:
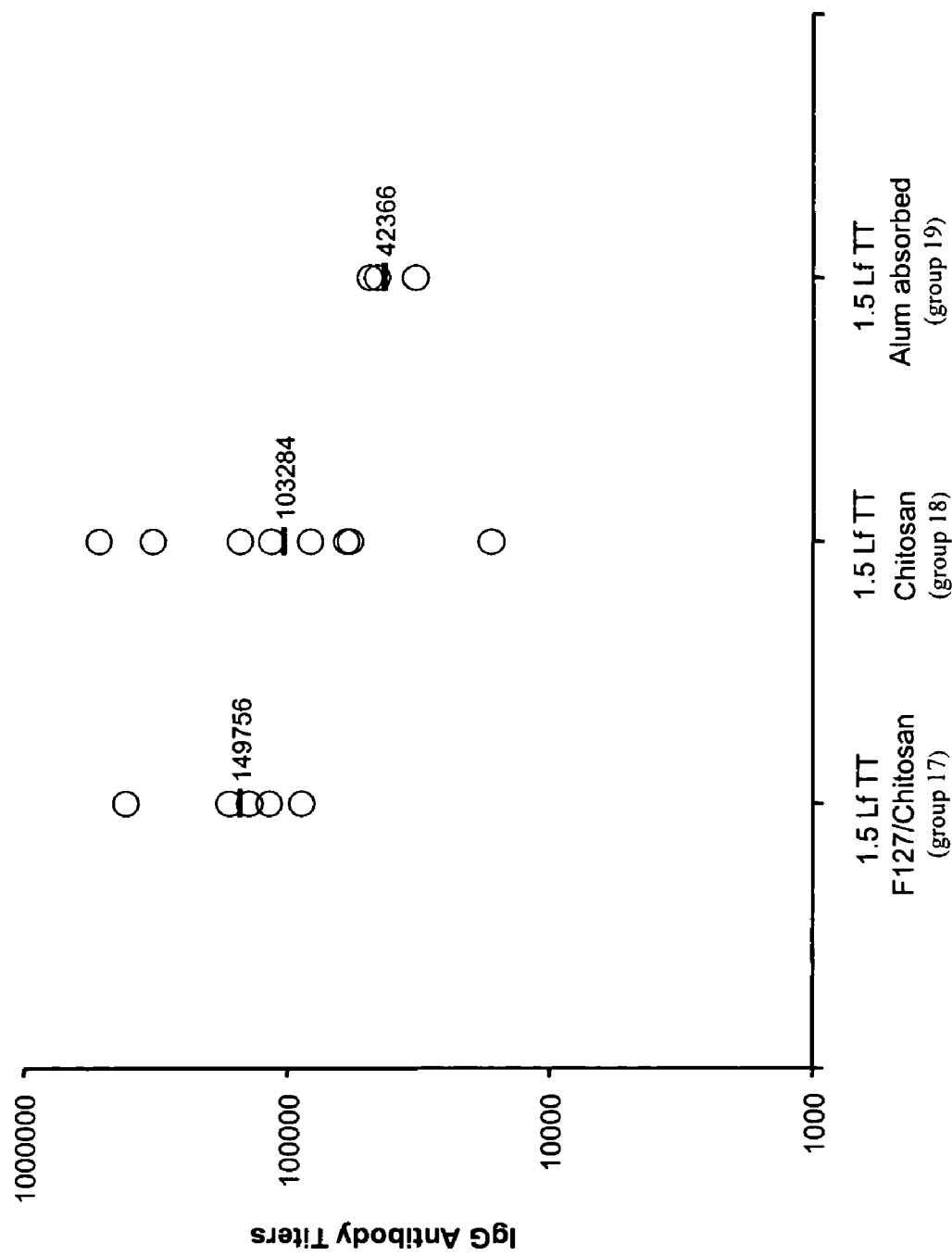
FIG. 8 is a graph of the antibody response in outbred mice 4 weeks after a single s.c. injection of 1.5 LfTT in various formulations.

Response in outbred mice. Groups of outbred, CD-1, female mice (n=8) (Harlan, Indianapolis, Ind.) were immunized once with 1.5 LfTT in F127/chitosan or with 1.5 LfTT mixed with chitosan alone. Methods for preparation of the formulations were similar to those described in Example 1, except that the final concentration of TT in the formulation was 15 Lf/ml and 0.1 ml per mouse was injected. In addition a group of mice (n=3) were immunized once a month for three months with 1.5 LfTT adsorbed to alum so that a comparison could be made with a standard immunization regimen. The mice immunized with TT plus chitosan with or without F127 generated a robust and prolonged IgG anti-TT antibody response after a single injection. These responses were higher than that to TT on alum; the response to TT/alum did not achieve the same levels as those elicited by either formulation until at least 2 injections of alum had been administered (FIG. 7). However it is important to note that for the first two weeks the response elicited by TT/F127/chitosan was significantly higher than that elicited by TT/chitosan (week 1: $p=0.028$ and week 2: $p=0.05$). Moreover the intragroup variability at 4 weeks was much less in the group of mice receiving TT/F127/chitosan than in the group receiving TT/chitosan only (see FIG. 8). This indicates a significant advantage in the use of F127 in the formulation and agrees with data shown in Example 5 in which chitosan and F127/chitosan were compared using the intranasal route.

TABLE 7

| Group | TT Immunization Formulation and Administration Route at Month 0 | TT Boost Form./Admin. Months 2 and 3 |
|---|---|---|
| 17 | 1.5 LfTT/F127/Chitosan, s.c. | none |
| 18 | 1.5 LfTT/Chitosan, s.c. | none |
| 19 | 1.5 LfTT on alum, s.c. | 1.5 LfTT on alum, s.c. |

Example 8

The methods used in this example were the same as those described in Example 3, except as noted.

Figure 9:
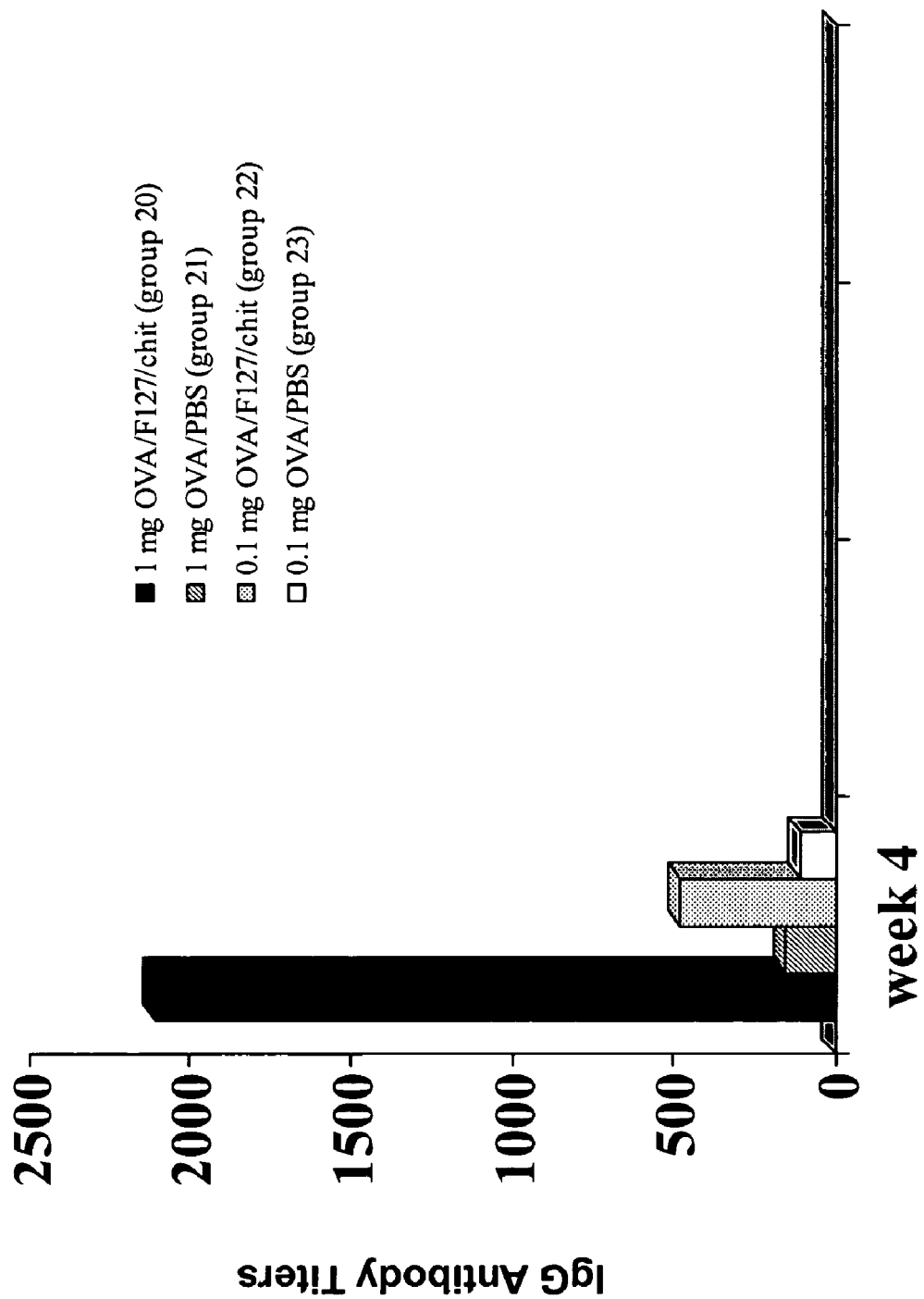
FIG. 9 is a graph of the IgG anti-chicken ovalbumin (OVA) antibody response in inbred mice after one s.c. immunization with either 1 milligram (mg) or 0.1 mg of OVA in either F127/chitosan or PBS.
Figure 10:
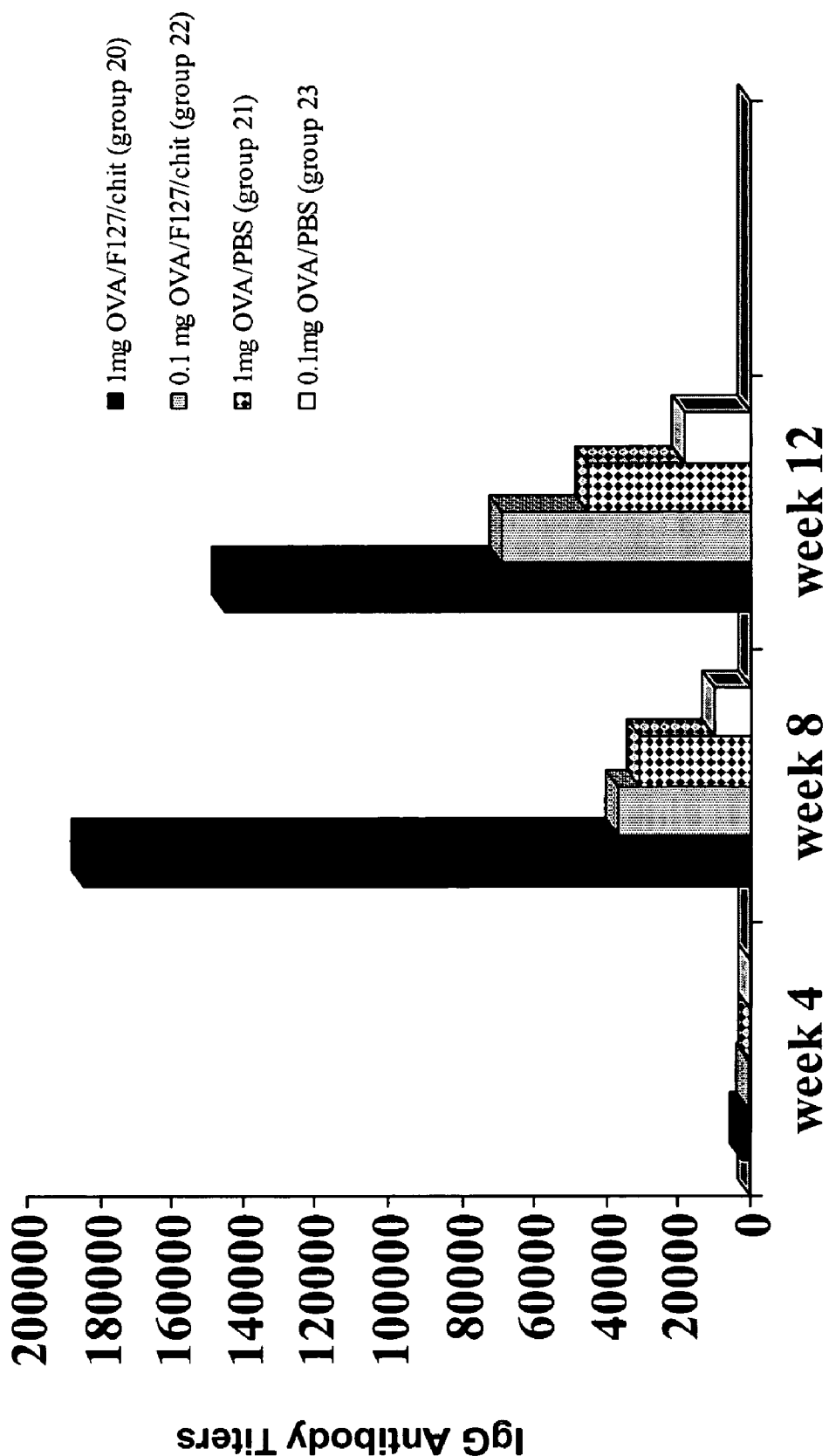
FIG. 10 is a graph of the IgG anti-OVA antibody response in inbred mice after two s.c. immunizations with either 1 mg or 0.1 mg of OVA in either F127/chitosan or PBS.

Elicitation of IgG antibody response to chicken ovalbumin. Groups of Balb/c female mice were immunized s.c. at day 0 and day 30 with either 1 mg or 0.1 mg chicken ovalbumin (OVA) (Sigma-Aldrich) formulated either in F127/chitosan or in PBS. Methods for preparation of the formulations were similar to those described in Example 3 except that they were prepared with OVA at a final concentration of 10 mg/ml or 1 mg/ml and 0.1 ml per mouse was injected. Serum samples were collected at various time points and analyzed for the presence of IgG anti-OVA antibodies by ELISA as described in Example 3 but using 10 ug/ml of OVA to coat the plates. It was found (see FIG. 9) that 4 weeks after a single injection, the IgG anti-OVA response in mice that received 1 mg OVA/F127/chitosan was significantly higher than that of mice receiving 1 mg OVA in PBS ($p=0.002$). At four weeks, all mice received a second injection of the same formulation and the antibody responses to OVA were measured four and eight weeks after this boost (see FIG. 10). The response to 1 mg OVA/F127/chitosan was still significantly higher than that to OVA/PBS ($p=0.015$) and furthermore the response to 0.1 mg of OVA/F127/chitosan was now also significantly higher than that to OVA in PBS eight weeks after the boost ($p=0.007$).

TABLE 8

| Group | OVA Prime Formulation and Administration Route, Day 0 | OVA Boost Form./Admin. Week 4 |
|---|---|---|
| 20 | 1 mg OVA/F127/Chitosan, s.c. | 1 mg OVA/F127/Chitosan, s.c. |
| 21 | 1 mg OVA/PBS (Control), s.c. | 1 mg OVA/PBS (Control), s.c. |
| 22 | 0.1 mg OVA/F127/Chitosan, s.c. | 0.1 mg OVA/F127/Chitosan, s.c. |
| 23 | 0.1 mg OVA/PBS (Control), s.c. | 0.1 mg OVA/PBS (Control), s.c. |

Example 9

The methods used in this example were the same as those described in Example 3, except as noted.

Figure 11:
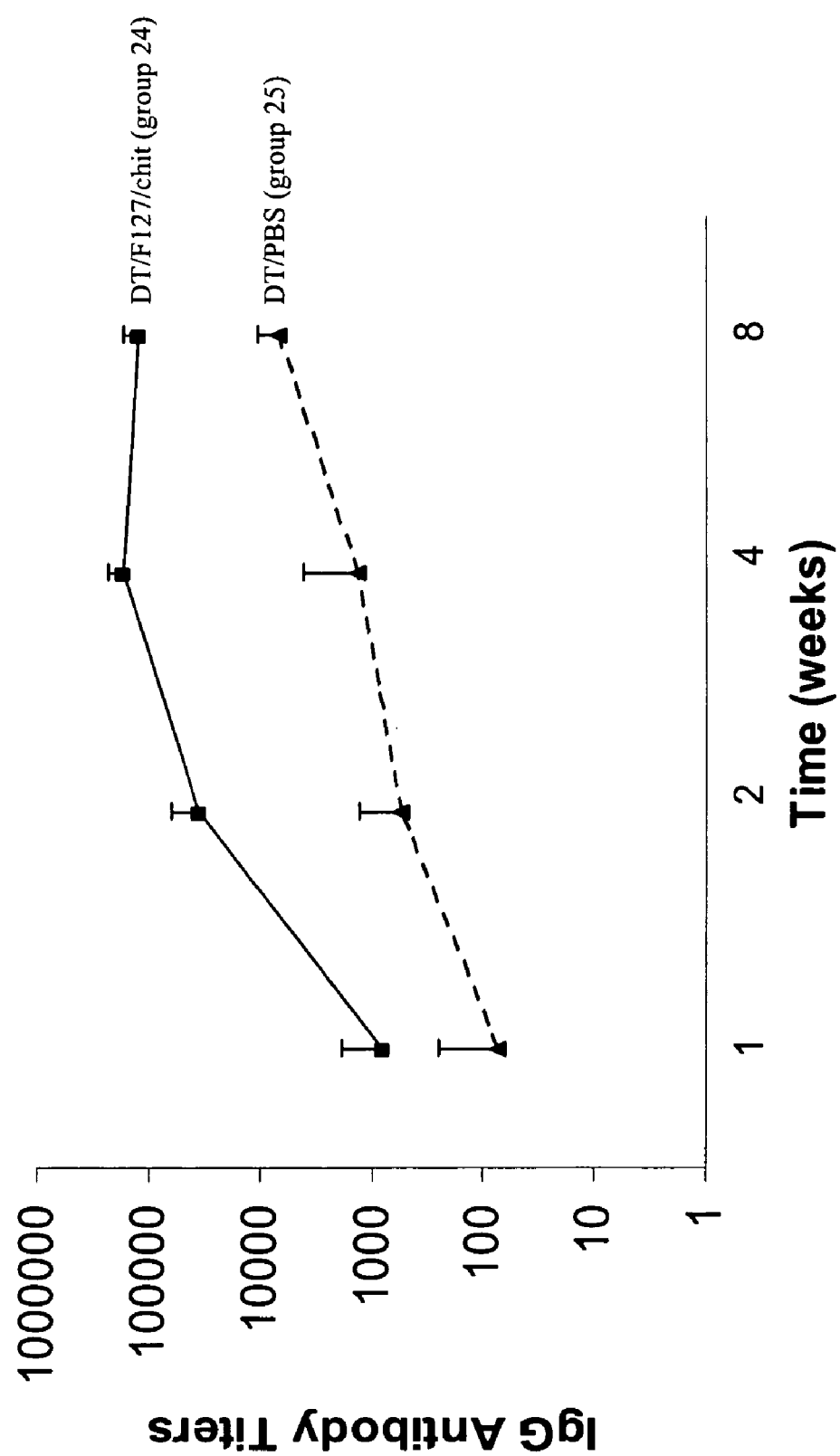
FIG. 11 is a graph of the IgG anti-diphtheria toxoid (DT) antibody response in outbred mice after a single s.c. immunization with 5 LfDT in either DT/F127/chitosan (■) or DT/PBS (▲).

Elicitation of IgG antibody response to diphtheria toxoid (DT). Groups of outbred CD-1 female mice (n=7) were immunized once s.c. with different doses of DT (approximately 1875 Lf/mg protein nitrogen, obtained from the National Institute for Biological Standards and Control [NIBSC], Potters Bar, Herts, UK) formulated either in F127/chitosan or in PBS. Methods for preparation of the formulations were similar to those described in Example 3 except that formulations contained 50 Lf/ml of DT and 0.1 ml per mouse was injected. Serum samples were collected at weeks 1, 2, 4 and 8 and analyzed for the presence of IgG anti-DT antibodies by ELISA as described in Example 3 except that 1 ug/ml DT was used to coat the wells of microwell plates. The IgG anti-DT antibody response looked similar to that of TT inasmuch as the IgG appeared rapidly (within one week) and continued to increase rapidly for at least 4 weeks after a single immunization (see FIG. 11).

TABLE 9

| Group | DT Single Injection Formulation and Administration Route |
|---|---|
| 24 | 5 LfDT/F127/Chitosan, s.c. |
| 25 | 5 LfDT/PBS (Control), s.c. |

Example 10

Figure 12:
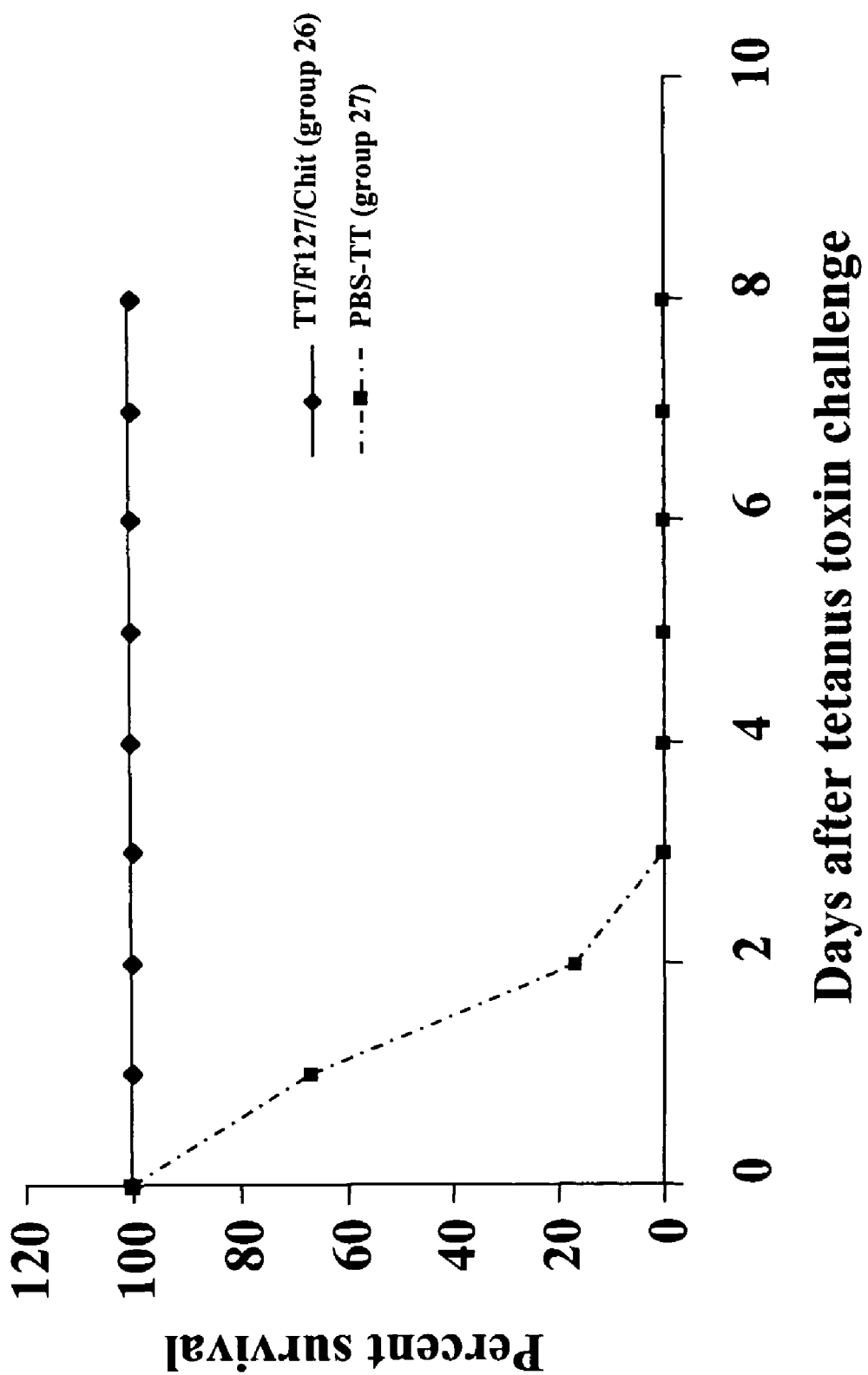
FIG. 12 is a graph of survival of inbred mice over an eight day period after being immunized once i.p. with 0.5 LfTT in F127/chitosan or in PBS and then challenged 6 weeks later i.p. with 100×LD$_{50}$ of tetanus toxin.

Protection of mice from lethal challenge with tetanus toxin. Groups of Balb/c female mice (n=8) were immunized once i.p. with 0.5 LfTT in F127/chitosan or in PBS. Six weeks after this single injection, mice were challenged i.p. with 100× LD$_{50}$ tetanus toxin (List Biological Laboratories Inc., Campbell, Calif.). FIG. 12 shows the percent survival over an eight day period following challenge. Mice receiving TT/F127/chitosan were completely protected against this otherwise lethal challenge with 8 out of 8 mice surviving whereas all 8 animals in the TT/PBS group succumbed. Therefore protective immunity was induced by TT/F127/chitosan immunization.

TABLE 10

| Group | Single Injection Formulation and Administration Route | Challenge Form./Admin. Week 6 |
|---|---|---|
| 26 | 0.5 LfTT F127/Chitosan, i.p. | Tetanus toxin, 100 × $LD_{50}$ |
| 27 | 0.5 LfTT/PBS, i.p. | Tetanus toxin, 100 × $LD_{50}$ |

While various specific embodiments of the present invention are described in detail, it should be recognized that the features described with respect to each embodiment may be combined in any combination with features described with respect to any other embodiment, to the extent that the features are not necessarily incompatible. Also, while various embodiments of the present invention have been described in detail, it is apparent that modifications and adaptations of those embodiments will occur to those skilled in the art. It is to be expressly understood that such modifications and adaptations are within the scope of the present invention, as set forth in the claims below and to the extent as permitted by the prior art.

What is claimed is:

1. A composition for delivery of an antigen for stimulation of an immune response when administered to a host, the composition comprising:

an antigen, a polyoxyalkylene block copolymer and an aqueous liquid;

the polyoxyalkylene block copolymer being biocompatible, not having toxic or injurious effects on biological function in the host when the composition is administered;

wherein, the composition is formulated with relative proportions of the liquid and the copolymer so that the copolymer interacts with the liquid to impart reverse thermal viscosity behavior to the composition, so that the viscosity of the composition increases when the temperature of the composition increases over some temperature range within 1° C. to 37° C.; and wherein, the composition further comprises an additive enhancing the immune response when the composition is administered to the host, the additive being an adjuvant other than alum; and;

wherein, the liquid comprises from 60 weight percent to 85 weight percent of the composition, the antigen comprises from 0.0001 weight percent to 5 weight percent of the composition, the copolymer comprises from 5 weight percent to 33 weight percent of the composition and the additive comprises from 0.01 weight percent to 10.0 weight percent of the composition.

2. The composition of claim 1, wherein the composition is in the form of a flowable medium when the composition is at a first temperature in the temperature range and the composition is in a gel form when the composition is at a second temperature in the temperature range, the second temperature being higher than the first temperature.

3. The composition of claim 2, wherein the first temperature is in a range of from 1° C. to 20° C.

4. The composition of claim 2, wherein the first temperature is in a range of from 1° C. to 20° C. and the second temperature is in a range of from 25° C. to 37° C.

5. The composition of claim 2, wherein the copolymer is substantially all dissolved in the liquid when the composition is at the first temperature, and at least a portion of the copolymer comes out of solution in the liquid when the temperature of the composition is raised from the first temperature to the second temperature.

6. The composition of claim 1, wherein the polyoxyalkylene block copolymer comprises at least one block of a first polyoxyalkylene and at least one block of a second polyoxyalkylene.

7. The composition of claim 6 wherein the first polyoxyalkylene is polyoxyethylene and the second polyoxyalkylene is polyoxypropylene.

8. The composition of claim 7, wherein the polyoxyalkylene block copolymer has the formula:

$$HO(C_2H_4O)_b(C_3H_6O)_a(C_2H_4O)_bH$$

wherein a and each b are independently selected integers.

9. The composition of claim 8, wherein the $(C_2H_4O)_b$ blocks together comprise at least 70 weight percent of the polyoxyalkylene block copolymer.

10. The composition of claim 8 wherein a is between 15 and 80 and each b is independently between 50 and 150.

11. The composition of claim 7, wherein the polyoxyalkylene block copolymer has the formula:

$$H(OCH_2CH_2)_b(O\underset{\displaystyle CH_3}{\overset{|}{C}}HCH_2)_a(OCH_2CH_2)_bOH$$

wherein a is 20 to 80 and each b is independently 15 to 60.

12. The composition of claim 1, wherein the antigen is selected from the group consisting of bacteria, protozoa, fungus, hookworm, virus and combinations thereof.

13. The composition of claim 1, wherein the antigen is selected from the group consisting of tetanus toxoid, diphtheria toxoid, a non-pathogenic mutant of tetanus toxoid, a non-pathogenic mutant of diphtheria toxoid and combinations thereof.

14. The composition of claim 1, wherein the antigen is from *Bordatella pertussis.*

15. The composition of claim 1, wherein the antigen is from influenza virus.

16. The composition of claim 1, wherein the antigen is from *M. tuberculosis.*

17. The composition of claim 1, wherein the antigen immunizes against a childhood illness.

18. The composition of claim 1, wherein the antigen is from rotavirus.

19. The composition of claim 1, wherein the antigen is selected from the group consisting of a polysaccharide, a peptide mimetic of a polysaccharide, an antigen from *Neisseria meningitiditis*, an antigen from *Streptococcus pneumoniae* and combinations thereof.

20. The composition of claim 1, wherein the antigen is from Epstein-Barr virus.

21. The composition of claim 1, wherein the antigen is from Hepatitis C virus.

22. The composition of claim 1, wherein the antigen is from HIV.

23. The composition of claim 1, wherein the antigen comprises a molecule involved in a mammalian reproductive cycle.

24. The composition of claim 1, wherein the antigen is HCG.

25. The composition of claim 1, wherein the antigen is a tumor-specific antigen.

26. The composition of claim 1, wherein the antigen is from a blood-borne pathogen.

27. The composition of claim 1, wherein the antigen is a first antigen and the composition comprises a second antigen.

28. The composition of claim 27, wherein the first antigen is selected from the group consisting of tetanus toxoid, a nonpathogenic mutant of tetanus toxoid and combinations thereof; and
the second antigen is selected from the group consisting of diphtheria toxoid, a nonpathogenic mutant of diphtheria toxoid and combinations thereof.

29. The composition of claim 1, wherein the adjuvant comprises dimethyl dioctadecyl ammonium bromide (DDA).

30. The composition of claim 1, wherein the adjuvant comprises a CpG motif.

31. The composition of claim 1, wherein the adjuvant comprises a cytokine.

32. The composition of claim 1, wherein the adjuvant comprises chitosan material.

33. The composition of claim 32, wherein the adjuvant comprises N,O-carboxymethyl chitosan.

34. The composition of claim 1, wherein the composition is in the form of disperse droplets in a mist.

35. The composition of claim 34, wherein the mist is produced by a nebulizer.

36. The composition of claim 1, wherein the composition is contained within a nebulizer actuatable to produce a mist comprising dispersed droplets of the composition.

37. The composition of claim 35, wherein the nebulizer is a nasal nebulizer.

38. The composition of claim 1, wherein the composition is contained within an injection device that is actuatable to administer the composition to the host by injection.

39. A method of packaging and storing the composition of claim 3, comprising placing the composition in a container when the composition is in the form of a flowable medium and, after the placing, raising the temperature of the composition in the container to convert the composition to the gel form for storage, wherein the gel form in the container can be converted back to the form of a flowable medium for administration to the host by lowering the temperature of the composition in the container.

40. The composition of claim 1, wherein substantially all of the copolymer is dissolved in the liquid at some temperature within the temperature range.

41. The composition of claim 1, wherein substantially all of the copolymer and the antigen are dissolved in the liquid at some temperature within the temperature range.

* * * * *